United States Patent [19]
Green et al.

[11] Patent Number: 6,066,622
[45] Date of Patent: May 23, 2000

[54] IMMUNOMODULATING PEPTIDES AND METHODS OF USE

[75] Inventors: Lawrence R. Green, Tacoma, Wash.; Nicolay V. Sinackevich, St. Petersburg, Russian Federation; Vadim T. Ivanov, Moscow, Russian Federation; Inessa I. Mikhalyova, Moscow, Russian Federation; Boris V. Vaskovsky, Moscow, Russian Federation; Alexander N. Mikhaltsov, St. Petersburg, Russian Federation; Vladimir K. Khavinson, St. Petersburg, Russian Federation; Vyacheslav G. Morozov, St. Petersburg, Russian Federation

[73] Assignee: Cytran, Inc., Kirkland, Wash.

[21] Appl. No.: 08/144,779

[22] Filed: Oct. 28, 1993

Related U.S. Application Data

[63] Continuation-in-part of application No. 07/967,633, Oct. 28, 1992, and a continuation-in-part of application No. 07/783, 517, Oct. 28, 1991, and a continuation-in-part of application No. 07/816,205, Jan. 2, 1992.

[51] Int. Cl.[7] .................................................. A61K 38/00
[52] U.S. Cl. ................................. 514/17; 514/15; 514/16
[58] Field of Search ................................. 514/13, 14, 15, 514/16, 17, 18

[56] References Cited

U.S. PATENT DOCUMENTS

| | | |
|---|---|---|
| 4,002,602 | 1/1977 | Goldstein . |
| 4,010,148 | 3/1977 | Goldstein . |
| 4,077,949 | 3/1978 | Goldstein . |
| 4,079,127 | 3/1978 | Goldstein et al. . |
| 4,116,951 | 9/1978 | Wang . |
| 4,120,951 | 10/1978 | Goldstein . |
| 4,133,804 | 1/1979 | Bach et al. . |
| 4,148,788 | 4/1979 | Wang . |
| 4,167,557 | 9/1979 | Goldstein . |
| 4,261,886 | 4/1981 | Goldstein et al. . |
| 4,264,571 | 4/1981 | Goldstein et al. . |
| 4,297,276 | 10/1981 | Goldstein et al. . |
| 4,339,427 | 7/1982 | Goldstein et al. . |
| 4,353,821 | 10/1982 | Birr et al. . |
| 4,374,828 | 2/1983 | Folkers et. al. . |
| 4,377,511 | 3/1983 | Lopukhin et al. . |
| 4,388,234 | 6/1983 | Horecker . |
| 4,389,343 | 6/1983 | Horecker . |
| 4,395,404 | 7/1983 | Low et al. . |
| 4,396,605 | 8/1983 | Birr . |
| 4,426,324 | 1/1984 | Meienhofer . |
| 4,427,783 | 1/1984 | Newman et al. . |
| 4,428,938 | 1/1984 | Kisfaludy et al. . |
| 4,442,031 | 4/1984 | Felix et al. . |
| 4,466,918 | 8/1984 | Birr et al. . |
| 4,470,926 | 9/1984 | Birr et al. . |
| 4,500,450 | 2/1985 | Seipke et al. . |
| 4,505,853 | 3/1985 | Goldstein et al. . |
| 4,517,119 | 5/1985 | Felix et al. . |
| 4,526,717 | 7/1985 | Seipke et al. . |
| 4,571,336 | 2/1986 | Houck et al. . |
| 4,599,231 | 7/1986 | Milich et al. . |
| 4,612,365 | 9/1986 | Birr et al. . |
| 4,614,731 | 9/1986 | Horecker . |
| 4,621,135 | 11/1986 | Trainin et al. . |
| 4,634,682 | 1/1987 | Erickson et al. . |
| 4,659,694 | 4/1987 | Horecker . |
| 4,696,915 | 9/1987 | Horecker . |
| 4,699,898 | 10/1987 | Gottlieb . |
| 4,711,952 | 12/1987 | Kasafirek et al. . |
| 4,722,999 | 2/1988 | Handschumacher et al. . |
| 4,751,216 | 6/1988 | Gottlieb . |
| 4,814,434 | 3/1989 | Goldfarb . |
| 4,826,680 | 5/1989 | Jaeger . |
| 4,904,643 | 2/1990 | Brunetti et al. . |
| 4,910,296 | 3/1990 | Birr et al. . |
| 4,983,387 | 1/1991 | Goldstein et al. . |
| 7,415,283 | 12/1988 | Yakovlev et al. . |

FOREIGN PATENT DOCUMENTS

| | | |
|---|---|---|
| 0 164 654 | 5/1985 | European Pat. Off. . |
| SU8800255 | 7/1989 | European Pat. Off. . |
| 2583982 | 1/1987 | France . |
| 3421789 | 10/1988 | Germany . |
| 1 363 801 | 8/1974 | United Kingdom . |

OTHER PUBLICATIONS

CA 78: 43980, 1973, Bennett et al. R.S.Chen, CA 111: 55230r, 1989.
Hirschmann et al., CA 79:66820e, 1973.
Giori et al., CA 89: 215752v, 1978.
Cola et al., CA 111: 129603p, 1989.
Anisimov et al. (1982) *Mechanisms of Ageing and Development*, 19:245–258.
Anisimov et al. (1989) *Mechanisms of Ageing and Development*, 49:245–257.
Belokrylov et al. (1978) *Bulletin of Experimental Biology*, No. 7, 84:56–58.
Bespaluv et al. (1989) *Eksp. Onkol.*, Chemical Abstracts III, Abstract No. 146389R, 11(4) 23–6 (Russ).
Cytomedins (Bulletin), Apr. 13, 1990, Russia.
Gavrilenko et al. (1982) *Bulletin of Experimental Biology*, No. 4, 93:39–40.
Goldstein et al. (1972) *Proc. Natl. Acad. Sci. USA*, 69:1800–1803.
R. S. Chen (1989) *Chemical Abstracts*, Vol. 111(7), Abstract No. 55230R.
Fauszt et al. (1975) *Chemical Abstracts*, Vol. 82(11), Abstract No. 73453C.
Khmel'nitskii et al. (1983), *Bulletin of Experimental Biology*, No. 6, 95:123–124.

(List continued on next page.)

Primary Examiner—Avis M. Davenport
Attorney, Agent, or Firm—Townsend and Townsend and Crew

[57] ABSTRACT

This invention provides methods of modulating the immune system by administering peptides of the formula R'-Glx-Glx-Lys-R" (SEQ ID NO:1) in which Glx is Glu or Gln. In particular, this invention provides the use of peptides Thr-Ala-Glu-Glu-Lys (SEQ ID NO:34) and Thr-Pro-Glu-Glu-Lys (SEQ ID NO:33).

36 Claims, 10 Drawing Sheets

OTHER PUBLICATIONS

Kuznik et al. (1982), *Bulletin of Experimental Biology*, No. 9, 94:27–29.

Kusnik et al. (1981) *Bulletin of Experimental Biology*, No. 9, 92:264–266.

Low et al. (1981) *Proceedings of the National Academy of Science*, 78:1162–1166.

Rodionov et al. (1990) "The Immunocorrective Therapy of Pyoderma Caused by Staphylococci Multiply Resistant to Antibiotics", *Vestn. Dermatol. Venerol*, 1:42–45 (Medline Abstract No. 90224329).

Solov'ev et al. (1977) *Bulletin of Experimental Biology*, No. 9, 84:355–358.

Solov'ev et al. (1983) *Bulletin of Experimental Biology*, No. 6, 95:123–124.

"Thymogen"(Bulletin ), Nov. 11, 1989, published by Cytomed (Leningrad).

Yakovlev et al., (1990) Resistance Stress Regulation, Nauka Publishers (Leningrad), pp. 90–93, 174–205.

Two brochures in Russian (no English translation).

*Remington's. Pharmaceutical Science*, 17th ed., Mack Publishing Co., Easton, PA (1985).

Stewart and Young, *Solid Phase Peptide synthesis*, 2nd ed., Pierce Chemical Company (1984).

Maniatis et al., (1982) *Molecular Cloning*, A Laboratory Manual, Cold Spring Harbor Laboratory.

Tam et al. (1983) *J. Am. Chem. Soc.*, 105:6442.

Declaration of Lawrence R. Green.

*50 TROUT INOCULATED WITH VIBRIO ANGUILLARUM 7 DAYS AFTER A 5 MINUTE EXPOSURE TO TEST ARTICLE IN A 38 LITER TANK PER STUDY GROUP

*50 TROUT INOCULATED WITH VIBRIO ANGUILLARUM 7 DAYS AFTER A 5 MINUTE EXPOSURE TO TEST ARTICLE IN A 38 LITER TANK PER STUDY GROUP

# IMMUNOMODULATING PEPTIDES AND
METHODS OF USE

This is a continuation-in-part of (1) copending Ser. No. 07/967,633, filed Oct. 28, 1992; (2) copending Ser. No. 07/783,517, filed Oct. 28, 1991; and (3) copending Ser. No. 07/816,205, filed Jan. 2, 1992; each of which are incorporated herein by reference.

The present invention is directed to peptide pharmaceutical compositions and uses thereof, in particular, small peptides including the amino acid sequence, Glx-Lys. These peptide compositions are useful for modulation of the immune system; the treatment of immunodepressed states and of opportunistic infections in immunodepressed states associated with acquired immune deficiency syndrome; treatment of infections caused by bacterial, viral, fungal, and parasitic organisms; augmentation of vaccination response; treatment of atopic states, treatment of anemias; treatment of leukocytic disorders; and the like.

BACKGROUND OF THE INVENTION

A wide variety diseases are caused by abnormalities of the immune system and hematological systems of animals including man. Further, the immune system is required to treat many other diseases. For example, immunodeficiencies such as the acquired immunodeficiency syndrome (AIDS) most commonly cause premature death and disability by making the person susceptible to infections and malignancies. This susceptibility is caused by a weakening of the immune system. Specifically, the HIV virus that causes AIDS attacks and kills T helper cells. Loss of T helper cells compromises the host's ability to fight infections by normal immunological mechanisms. Many types of malignancy are also associated with immunodeficient states suggesting that they are caused by a failure of normal host immune surveillance systems. Many diseases cause secondary immunodeficiency allowing for more rapid progression of the primary disease or the development of secondary diseases. Methods to enhance suppressed immune systems have not achieved high levels of efficacy.

Diseases may also be caused by hyperactivity of the immune system. For example, collagen vascular diseases are associated with immunologically-mediated damage to the host tissue. Such diseases include multiple sclerosis, rheumatoid arthritis and the like. These diseases afflict many individuals and cause significant morbidity and mortality. Treatments generally include immune suppression. Unfortunately, generalized immune suppression often results in increased incidence of infections and malignancies. Therefore, to treat one disease patients are placed at risk for developing other, possibly life threatening, diseases.

Immunological stimulation, even in healthy individuals, may aid in the treatment of several diseases. Infectious diseases may be more effectively treated by stimulation of the immune system. The enhanced immunological response may work with other treatments to eliminate the infection more readily. Also, specific immune stimulation has been shown to reduce tumor size in some malignancies. Also, many drugs used for primary treatment of infections and malignancies have significant side effects. Therefore, it is desirable to reduce the dose of the primary drug whenever possible.

What is needed in the art are compositions and methods for modulating the immune system. Ideally, these compounds and methods would be able to stimulate suppressed or deficient immune systems as well as reduce immune hyperactivity. Also these compounds and methods should act to restore a natural balance to the immune system. Quite surprisingly, the present invention fulfills these and other related needs.

SUMMARY OF THE INVENTION

The present invention provides compositions comprising a peptide having the formula R'-Glx-Glx-Lys-R" (SEQ ID NO:1) or a pharmaceutically acceptable salt thereof; wherein Glx is Glu or Gln; R' is H- or a first amino acid sequence having fewer than 7 amino acids; R" is -H or a second amino acid sequence having fewer than 7 amino acids; and the peptide has a sequence of at least 5 and not more than 9 amino acids. Generally, R' is H-, Thr-Ala-, Thr-Pro-, Ser-Ala-, Ser-Pro-, Ser-Ser-, Met-Leu-Thr-Ala- (SEQ ID NO:32), or Leu-Thr-Ala-; and R" is -H, -Ala, -Ala-Ala or -Ala-Val (SEQ ID NOS:2–31). In preferred embodiments, the peptide is L-Thr-L-Pro-L-Glu-L-Glu-L-Lys (SEQ ID NO:33) or L-Thr-L-Ala-L-Glu-L-Glu-L-Lys (SEQ ID NO:34).

Also provided are pharmaceutical preparations comprising a peptide having the formula R'-Glx-Lys-R' (SEQ ID NO:35) or a pharmaceutically acceptable salt thereof, wherein Glx is Glu or Gln; R' is H- or a first amino acid sequence having fewer than 7 amino acids; R" is -H or a second amino acid sequence having fewer than 7 amino acids; and the peptide has a sequence of at least 2 and not more than 9 amino acids; and a physiologically acceptable carrier. In preferred embodiments, the peptide is L-Glu-L-Lys, L-Thr-L-Ala-L-Glu-L-Glu-L-Lys (SEQ ID NO:34) or L-Thr-L-Pro-L-Glu-L-Glu-L-Lys (SEQ ID NO:33).

Methods for using the peptides of the present invention are also provided. These methods include administration of the pharmaceutical preparations of the present invention for immunomodulation of a host's immune system, treatment of infections, treatment of anemias, treatment of atopic states, and treatment of leukocytic disorders.

DESCRIPTION OF THE PREFERRED EMBODIMENT

Figure 1:
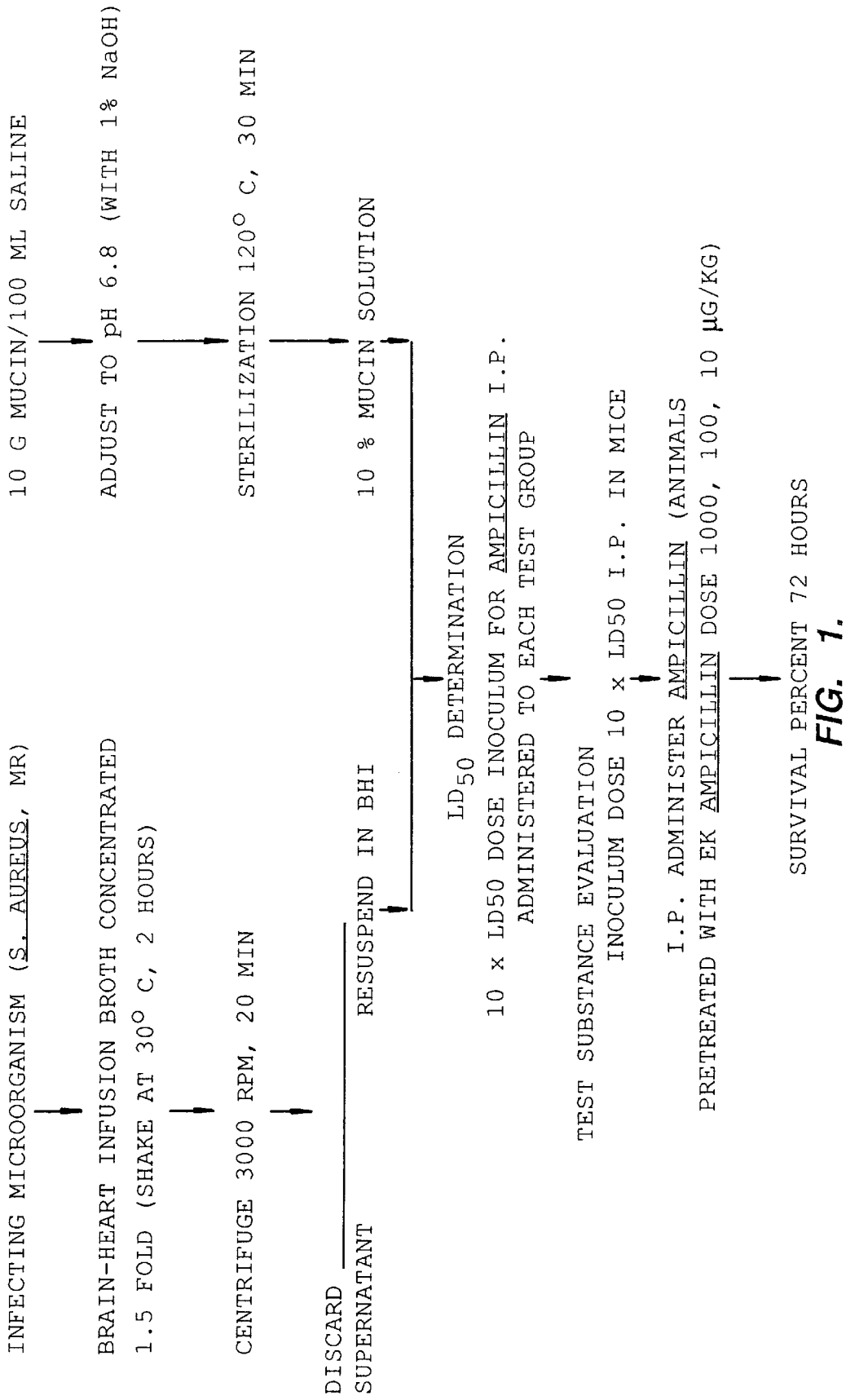
FIG. 1 illustrates an experimental method for assessing treatment of infection with EK.

The present invention is based in part on the discovery that certain peptide compositions exhibit a broad range of efficacy for modulation of the immune system. This provides a means for the prevention and treatment of infections in immunocompetent as well as immunodepressed states, and for therapeutically effective treatment of immunodeficient states, particularly AIDS. Other disorders associated with immune and hematologic systems may be similarly treated. This is believed to be highly unexpected for such relatively small compounds to exhibit such a broad range of activity. Furthermore, we have not found any significant side effects from the use of the peptides according to the present invention. Due to their simple nature, the peptides of the present invention are relatively inexpensive to manufacture.

The present invention provides peptide compositions, pharmaceutical preparations containing the peptides, and methods for therapeutic use of the peptides. Generally, the compositions comprise a peptide having the formula R'-Glx-Glx-Lys-R" (SEQ ID NO:1) or a pharmaceutically acceptable salt thereof; wherein Glx is Glu or Gln; R' is H- or a first amino acid sequence having fewer than 7 amino acids; R" is -H or a second amino acid sequence having fewer than 7 amino acids; and the peptide has a sequence of at least 5 and not more than 9 amino acids (SEQ ID NOS:2–31).

The pharmaceutical preparations of the present invention generally comprise a peptide having the formula R'-Glx-Lys-R" (SEQ ID NO:35) or a pharmaceutically acceptable salt thereof, wherein Glx is Glu or Gln; R' is H- or a first amino acid sequence having fewer than 7 amino acids; R" is -H or a second amino acid sequence having fewer than 7 amino acids; and the peptide has a sequence of at least 2 and not more than 9 amino acids; and a physiologically acceptable carrier. The peptides and pharmaceutical preparations may be employed in a variety of therapeutic uses. These include modulating the activity of a host's immune system, treating infections in a host, treating atopic states, treating leukocytic disorders, treating anemias in a host, and augmenting vaccination responses.

As used herein, the terms "immunomodulator" and "immunomodulating" encompass the activity of restoring the natural balance to a host's immune system. This includes enhancing or restoring the subject's immune system, as evidenced by measurable blood parameters and/or the patient's improved ability to combat infection or disease, and the ability to heal tissue. Hence, immunomodulation encompasses improvement of the immune system due to an immunodeficient state (for example, caused by removal of the thymus), and/or an immunodepressed state (for example, caused by exposure to radiation). Furthermore, the present invention provides for modulation of the immune system by lowering blood parameters and other indicia of the immune state if these indicia are abnormally elevated. The present invention encompasses the therapeutic method of treating the immunodeficient, immunodepressed or elevated immune state per se, thus providing prophylaxis against infection and disease, as well as a treatment of infection, disease or wound by enhancing the immune system.

Generally, the peptide will have formula of Formula I, using the normal convention wherein the first named amino acid is the amino terminus and the last named amino acid is the carboxyl terminus.

R'-Glx-Lys-R" (SEQ ID NO:35)  (I)

wherein:
R' is H-, Thr-Ala-Glx-, Thr-Pro-Glx-, Ser-Ala-Glx-, Ser-Pro-Glx-, Ser-Ser-Glx-, Met-Leu-Thr-Ala-Glx- (SEQ ID NO:38), or Leu-Thr-Ala-Glx- (SEQ ID NO:29);
R" is -H, -Ala, -Ala-Ala or -Ala-Val; and Glx is Glu or Gln (SEQ ID NOS:36, 37 and 2–31).

In accordance with a preferred embodiment of the present invention are pharmaceutical preparations comprising of the Formula II (Formula I wherein R"=H);

R'-Glx-Glx-Lys  (II)

wherein:
R' is Thr-Ala-Glx-, Thr-Pro-Glx-, Ser-Ala-Glx-; Ser-Pro-Glx-, or Ser-Ser-Glx- (SEQ ID NOS:4, 8, 12, 16 and 20, restpectively).

Preferred species are Glx-Lys and Thr-Ala-Glx-Glx-Lys (SEQ ID NO:4), particularly wherein Glx=Glu (SEQ ID NO:34). The amino acids of the peptides of the present invention may be either D or L stereoisomers. The amino acids in a peptide may all be either L or D or a mixture of L and D stereoisomers. It is generally preferred that all of the amino acids be of the L form. Specific amino acid stereoisomers will be denoted by a prefix of L- or D-. For example, the L stereoisomer of alanine is denoted L-Ala.

Species in which R"=H indicates a free C-terminus carboxyl group.

Other particularly preferred species useful in accordance with the invention are the peptides according to Formula I wherein:
R'=Glx- (SEQ ID NOS:36, 2 and 3)
R'=Thr- Pro-Glx- (SEQ ID NOS:8–11)
R'=Met-Leu-Thr-Ala-Glx- and R"=-Ala (SEQ ID NO:25);
R'=Leu-Thr-Ala-Glx- and R"=-Ala (SEQ ID NO:29);
R'=Leu-Thr-Ala-Glx- and R"=-Ala-Ala (SEQ ID NO:30);
R=Leu-Thr-Ala-Glx- and R"=-Ala-Val (SEQ ID NO:31).

The peptides of the present invention may be combined in pharmaceutical preparations for a variety of therapeutic uses. The preparations may be administered to a variety of hosts for therapeutic purposes. Suitable hosts include human and non-human primates, domestic animals including dogs, cats, rodents, birds, horses, cows, pigs, fish, and the like.

The compositions may also find use for pre- or post-exposure prophylaxis, e.g., HIV prophylaxis following "dirty needle" injuries to health care workers or routinely accompanying blood transfusions or to persons in danger of becoming exposed to infected body or culture fluids. The peptides of the present invention are particularly useful for augmentation of vaccinations. By "augmentation of vaccines", it is meant that the level and/or duration of complete or partial protection from disease obtained from vaccination is enhanced.

Administration of the peptides of the present invention is conjunction with a vaccine may enhance the immune response to the vaccine providing both a higher level of immunity and a prolonged anamnestic response. The peptides may be administered prior to, simultaneously with, or following vaccination. Generally, the peptides will be administered prior to or simultaneously with vaccination.

The pharmaceutical compositions are intended for parenteral, topical, oral, or local administration for prophylactic and/or therapeutic treatment. Preferably, the peptides of the present invention are administered intramuscularly or intranasally. As the peptides of the present invention may be administered parenterally, i.e., intravenously, subcutaneously, intramuscularly, or intrathecally, this invention provides pharmaceutical preparations for parenteral administration which comprise a solution of a peptide of the present invention dissolved in a pharmaceutically acceptable carrier, preferably an aqueous carrier. A variety of aqueous carriers may be used, e.g., water, buffered water, 0.4% saline, 0.3% glycine, and the like, including glycoproteins for enhanced stability, such as albumin, lipoprotein, globulin, etc. These compositions may be sterilized by conventional, well known sterilization techniques. The resulting aqueous solutions may be packaged for use or filtered under aseptic conditions and lyophilized, the lyophilized preparation being combined with a sterile aqueous solution prior to administration. The compositions may contain pharmaceutically acceptable auxiliary substances as required to approximate physiological conditions, such as pH adjusting and buffering agents, tonicity adjusting agents and the like, for example, sodium acetate, sodium lactate, sodium chloride, potassium chloride, calcium chloride, etc.

The active peptides of the pharmaceutical preparations according to the present invention may be used as free peptides or in the form of a water soluble pharmaceutically acceptable salt, such as a sodium, potassium, ammonium or zinc salt. In addition to the peptides and physiologically acceptable carriers, the pharmaceutical preparations may include other active ingredients which independently impart an activity to the composition, such as antibiotics, interferon, anesthetics, and the like.

The concentration of the peptides of the present invention in these pharmaceutical preparations can vary widely, i.e., from about 0.001% to as much as 15 or 20% by weight and will be selected primarily by fluid volumes, viscosities, etc., in accordance with the particular mode of administration selected. When utilized intramuscularly as an injection solution with the active ingredient in a therapeutically effective immunopotentiating amount of about 0.001 to 0.01% by weight. If prepared in the form of a tablet, capsule or suppository, it is preferred that the active ingredient be present in an amount of about 0.1 mg per tablet, suppository or capsule. In such form, the capsule, suppository or tablet may also contain other conventional excipients and vehicles such as fillers, starch, glucose, etc. Actual methods for preparing parenterally, orally, and topically administrable compounds will be known or apparent to those skilled in the art and are described in detail in, for example, Remington's Pharmaceutical Science, 17th ed., Mack Publishing Company, Easton, Pa. (1985), which in incorporated herein by reference.

Determination of an effective amount of peptide to treat hosts afflicted with different ailments may be determined through standard empirical methods which are well known in the art. For example, immunomodulation may be monitored by serial determinations of leukocyte count, sheep red blood cell erythrocyting activity, determination of relative and absolute levels of different leukocyte subsets (e.g., CD4 and CD8 subsets of T lymphocytes), sedimentation rates, C-reactive protein levels, immunoglobulin levels (particularly those directed at self-antigens), complement levels, and like, as well as general organ function of the host. Anemias may be monitored by serial determinations of hematocrit, hemoglobin, mean corpuscular volume, and the like. Well known methods of monitoring the treatment of infection include, e.g., culture and organ function indices. Atopic states may be evaluated by challenges to allergens and determination of IgE levels. Leukocytic disorders may be monitored by determination of white blood cell counts and leukocyte function assays. Vaccine augmentation may be monitored by repeated challenge of antigen, either virulent or attenuated, and observation of the host's immune response to the challenge.

Compositions of the invention are administered to a host already suffering from an infection, as described above, in an amount sufficient to cure or at least partially arrest the disease and its complications. An amount adequate to accomplish this is defined as "therapeutically effective dose." Amounts effective for this use will depend on the severity of the infection or disease and the weight and general state of the patient being treated, but generally range from about 0.001 mg/kg to about 5000 mg/kg host body weight of peptide per day, more commonly about 0.1 mg/kg to about 1000 mg/kg host body weight of peptide per day, usually about 0.25 mg/kg to about 100 mg/kg host body per day, more usually about 0.5 mg/kg to about 20 mg/kg host body weight per day, and preferably about 0.7 mg/kg to about 10 mg/kg host body weight per day. Maintenance dosages over a prolonged period of time may be adjusted as necessary. It must be kept in mind that the materials of the present invention may be employed in serious disease states, that is, life-threatening or potentially life threatening situations. In such cases, in view of the minimization of extraneous substances and general lack of immunogenicity when a human-derived polypeptide is employed to treat human hosts, it is possible and may be felt desirable by the treating physician to administer substantial excesses of these compositions. For veterinary uses higher levels may be administered as necessary while avoiding, however, undesirable toxicities.

In prophylactic applications, compositions containing the present invention are administered to a patient susceptible to or otherwise at risk for infection, anemia, or other disorder that may be treated by the methods of the present invention. Such an amount is defined to be a "prophylactically effective dose." In this use, the precise amounts again depend on the patient's state of health and weight, but are generally in the ranges described above for therapeutic use. Prophylactic administration may be particularly desirable for hosts that have been exposed or at risk for exposure of infectious diseases, e.g., health-care workers, travellers, family members of infected individuals, immunosuppressed persons, and the like. The peptides of the present invention may also be administered for surgical prophylaxis to lessen the risk of infectious complications and enhance the host's restorative response to blood loss.

Single or multiple administrations of the compositions can be carried out with the dose levels and pattern being selected by the treating physician or veterinarian. In any event, the pharmaceutical preparations should provide a quantity of sufficient to effectively treat, prevent, or inhibit disease in the host.

For the treatment of infection, the pharmaceutical preparations of the present invention may be administered alone or as adjunct therapy. The compositions may be administered with, e.g., antibiotics, anti-viral compounds, anti-fungal compounds, and anti-parasitic compounds. When employed to enhance a host's immune response to a tumor through immunomodulation, the peptides of the present invention may be administered with a variety of compounds for the treatment of malignancy. When administered as adjunct therapy, the compositions of the present invention may be administered in conjunction with the other treatment modalities, or separately at different intervals.

The peptides of the present invention may be synthesized by a variety of techniques well known in the art. Generally, the peptides will be prepared in solution or on a solid support by conventional peptide synthesis, including the Merrifield solid state peptide synthesis technique. For example, an amino and side chain protected derivative of an activated ester of Glx is reacted with side-group protected L-Lys, attached to the solid phase as its C-terminus. After elimination of the alpha-amino protecting group, the next amino acid is added in a similar fashion. Additional amino acids are serially added. The peptides are cleaved by highly acidic cleavage that also typically removes protecting groups. The peptides may then be isolated and lyophilized and stored for future use. Suitable techniques of peptide synthesis are described in detail in Stewart and Young, *Solid Phase Peptide Synthesis*, 2d edition, Pierce Chemical Company, 1984; and Tam et al., *J. Am. Chem. Soc.*, 105:6442 (1983), both of which are incorporated herein by reference.

Alternatively, hybrid DNA technology may be employed for expression of the desired peptide in transformed eukaryotic or prokaryotic host cells. See, for example, Maniatis et al., Molecular Cloning, A Laboratory Manual, Cold Spring Harbor Laboratory, 1982, incorporated herein by reference.

The present invention provides methods of using the compositions and preparations of the present invention. The methods generally comprise administering to the host a peptide having the formula R'-Glx-Lys-R" (SEQ ID NO:35) or a pharmaceutically acceptable salt thereof, wherein Glx is Glu or Gln; R' is H- or a first amino acid sequence having fewer than 7 amino acids; R" is -H or a second amino acid sequence having fewer than 7 amino acids; and the peptide has a sequence of at least 2 and not more than 9 amino acids. A therapeutic or prophylactic amount of the peptide will typically be administered. Generally either Glx-Lys and Thr-Ala-Glx-Glx-Lys (SEQ ID NO:4) will be employed in the claimed methods although other peptides may be used.

The method described above may be employed to modulate the activity of a host's immune system. The activity of the immune system may be enhanced or suppressed by the claimed methods. Immunological enhancement may occur following administration of the peptides to immunosuppressed or immunodeficient hosts. This may be employed as a treatment for a variety of primary disease states as well as secondary effects of diseases or treatments. For example, primary immunodeficiencies, such as the acquired immunodeficiency syndrome (AIDS), DeGeorge's syndrome, severe combined immunodeficiency, and the like, may be treated by these methods. Secondary immunodeficiencies, such as anergy from tuberculosis, drug-induced leukopenia, non-HIV viral illnesses leukopenia, radiation poisoning, toxin exposure, malnutrition, and the like, may be treated by immunomodulating the activity of a host's immune system. Enhancement of the host's immune system may aid in the therapy of a variety of diseases including, e.g., malignancies, infections, and the like.

Immunomodulation by the methods of the present invention may also be employed for the treatment of hyperactive immune states. Such hyperactive immune states include, e.g., systemic lupus erythematosis, rheumatic fever, rheumatoid arthritis, multiple sclerosis, and the like. Treatment with peptides as described above may restore the natural balance to the immune system and lessen or eliminate the immunological reaction to host tissue.

The methods may also be employed for the treatment of a variety of infections. These infections include bacterial infections, viral infections, fungal infections, and parasitic infections. Typical bacterial infections that may be treated by the methods of the present invention include, e.g., mycobacterial infections (e.g., tuberculosis, leprosy, *M. avium, M. intracellulare*), gram positive infections (e.g., Staphylococus, Streptococcus, and Listeria), gram negative infections (e.g., Pseudomonas), mycoplasma, spirochetal infections (e.g. syphilis), and the like. Both aerobic and anaerobic bacteria may be treated by the methods of the present invention.

Viral infections that may be treated by the methods of the present invention include HIV-1 and HIV-2, cytomegalovirus, herpes simplex virus Type I and Type II, Epstein-Barr virus, HTLV-I and HTLV-II, Marek's disease, hog cholera virus, feline sarcoma virus, distemper virus, and the like. Fungal infections, such as, e.g., *Candida albicans*, Histoplasmosis, Coccidiomycosis, Aspergillosis, and Cryptococcus may be treated by the methods of the present invention. Parasitic diseases including, e.g., malaria, schistosomiasis, toxoplasmosis, leishmaniasis, and pneumocystis, may be treated by the methods of the present invention.

As described above, the methods for treating infections will often include administration of an appropriate antibiotic, anti-viral compound, anti-fungal compound, or anti-parasitic compound. Persons of skill will readily appreciate how to make the selection of appropriate adjuvant therapy. Often, the methods of the present invention will allow for reduction of the dose of the adjuvant anti-infective employed. This may serve as a means to reduce or eliminate dose-related complications and side effects.

The methods of the present invention may also be used to treat atopic states. The peptides described above may modulate those components of the immune system responsible for allergic reactions. This may provide an effective treatment for diseases such as acute allergic reactions, chronic urticaria, and the like.

A variety of leukocytic disorders may also be treated by the methods of the present invention. Such disorders include pre-leukemias, leukemoid reactions, and the like. A variety of anemias may be treated by the methods of the present invention. These anemias include, acute hemorrhagic anemia, anemias of chronic disease, megaloblastic anemias, iron deficiency anemias, hemoglobinopathies, and the like.

The methods of the present invention may also indirectly enhance wound healing. This may occur by reducing local inflammation in the wound site and decreasing the risk of infection.

The following examples are offered by way of illustration and not limitation.

EXAMPLE 1

Effect of Immune System of Health Guinea Pigs

Forty male guinea pigs were used in the following test. Most of the animals were treated daily with a single dose (i.m.) of Thr-Ala-Glu-Glu-Lys (SEQ ID NO:34) (HM897) of microgram/kg for five days. Control animals were treated with single daily doses of 0.5 ml (i.m.) of normal saline.

Tested parameters: clinical blood examination, non-specific resistance by lysosomal cationic test;"active" T-lymphocytes and total T-lymphocytes (E-RFC), B-lymphocytes (EAC-RFC) were measured in blood, thymus, lymph nodes, spleen and red bone marrow. Blood lymphocyte functional activity was evaluated by leukocyte migration inhibition (LMI) with ConA. Histological examinations of thymus, lymph nodes, spleen and red bone marrow. Blood lymphocyte functional activity was evaluated by leukocyte migration inhibition (LMI) with ConA. Histological examinations of thymus, spleen, lymph nodes, bone marrow and adrenals were carried out. All of these indicia were measured on 10th and 20th days after onset of the treatment.

Principal findings: the peptide stimulates lymphoid cells proliferation and differentiation in thymus and bone marrow; on the 10th day the predominant T-lymphocyte stimulation is observed, on the 20th- both T- and B-lymphocytes. On the 10th day after onset of administration, the peptide causes increased level of mitotic activity in lymph notes, spleen, and especially bone marrow.

EXAMPLE 2

Effect on Immune System

Twenty-two male guinea pigs were used in the following test.

Guinea pigs were exposed to irradiation in a total does lGy.target-skin distance—70 cm; time of exposure—2'48" Device: 180 kV; 15 mA; filter 0.5 Cu Treatment: i.m. single daily 1 microg. HM897 per kg for 5 days.

Treatment of controls: normal saline 0.5 ml i.m. single daily for 5 days.

Leukocyte and lymphocyte levels were measured in peripheral blood on the 7th, 14th, 21st, 36th and 44th day after irradiation.

Principal findings: the peptide stimulated proliferation of blood lymphoid cells resulted in restoration of leukocyte and lymphocyte levels. In controls there were no immune cells restoration during all period of observation.

In a second test 40 male guinea pigs were used, and the same regimen was followed.

There were two controls—irradiated and non-irradiated. Parameters were evaluated on the 8th and 21st days after irradiation. Tested parameters: clinical blood examination, non-specific resistance by lysosomal cationic test; "active" T-lymphocytes and total T-lymphocytes (E-RFC), B-lymphocytes (EAC-RFC) were measured in blood, thymus, lymph nodes, spleen and red bone marrow. Blood lymphocyte functional activity was evaluated by leukocyte migration inhibition (LMI) with ConA. Histological examinations of thymus, spleen, lymph nodes, bone marrow and adrenals were carried out.

Principal findings: the peptide used in irradiated animals accelerates T-lymphocyte maturation and their migration to peripheral immune organs in early terms of observation. In the later stage of the study effects were more pronounced in the enhancement of proliferation and differentiation in both central and peripheral organs of the immune system. Administration restored peripheral blood lymphocytes and neutrophil functional activity.

EXAMPLE 3

Effects in Thymectomized Guinea Pigs

Model: Thymectomy (removal of thymus): 30 mongrel male guinea pigs.

Treatment: i.m. single daily 1 microg HMS97 per kg for 10 days.

Treatment of controls: normal saline 0.5 ml i.m. single daily for 10 days (there were two controls—thymectomized and sham-operated).

Parameters were determined on the 15th day after onset of the treatment.

Tested parameters: clinical blood examination, "active" T-lymphocytes and total T-lymphocytes (E-RFC), B-lymphocytes (EAC-RFC) were measured in blood, thymus, lymph nodes, spleen and red bone marrow.

Principal findings: the peptide use in thymectomized animals does not stimulate lymphoid cells differentiation, but, on the contrary, does suppress it to some degree.

EXAMPLE 4

Effect on Superficial Receptors Expression on T- and B-Lymphocytes

Model: A. This work was designed to study the restoration of superficial receptors on lymphocytes after proteolytic digestion or after severe secondary immunodeficiency. Thymocytes obtained from guinea-pig were trypsinized and then their rosette-forming capacity with rabbit erythrocytes (E-RFC) was evaluated. The cells were incubated with the peptide in concentrations 1, 10 and 100 microg/ml. There were two controls—intact thymocytes (not trypsinized) and trypsinized thymocytes not incubated with the. peptide.

Principal findings: The peptide was the most active in concentration 10 microg/ml—its biological activity made up 78/9% (percentage of rosette-forming capacity restoration).

B: B-lymphocytes were obtained from patients with streptococcal and staphylococcal skin disease showed highly pronounced secondary immunodeficiency. The number of cells carrying Ig-receptors before and after incubation with the peptide has been measured (by means for FITC-labelled sera against human Ig).

Principal findings: the peptide in concentration 1 microg/ml causes significant increase of cells carrying Ig-receptors of different types.

EXAMPLE 5

Erythropoietic Effects

This test was designed to study posthemorrhagic anemia (acute blood loss caused by taking blood from retroorbital sinus), and hemolytic anemia induced by phenylhydrazine hydrochloride (120 mg active ingredients/kg 30 Balb/c-mice and 30 CBA-mice).

HM897 was injected intraperitoneally in doses of 100 and 150 microg per kg, 3 hours and 1 day after intervention modelling anemia, for 5 days.

Tester parameters: RBC, leukocytes, reticulocytes, Hb, Hct

Principal findings: 1. in posthemorrhagic anemia the most pronounced alternations of tested parameters were observed on 4th–5th day after the invasion: erythrocytes dropped to 4.2 mln/ml vs. 6.2 mln/ml in control, reticulocytes, rose 3 times, leukocytes were also increased. After hg administration, on the 6th day, RBC count rose up to 7.1 mln/ml; Hb level and plasma/formed elements ration restoration were more rapid. The peptide was the most effective in dose 150 microg/kg.

2. In hemolytic phenylhydrazine-induced anemia the most pronounced hemodepression has arisen on the 7th day. RBC dropped to 3.8 mln/ml, Hb was diminished by 15%, reticulocytes have grown up to 15%. On the 3rd day of administration erythrocytes have increased up to 7.2 mln/ml and remained on this level in later terms. Thus, the peptide has erythropoietic effect in anemias of different genesis.

EXAMPLE 6

Influence on Colony-Forming Activity

This test is designed to study macrophage precursors. Cultured cells used were guinea-pig myelokaryocytes. HM897 was added to cell culture in concentrations 1.0, 0.001, 0.00001 and 0.0000001 microg/ml.

The peptide stimulates macrophage precursors colony-forming activity in concentration starting form 0.0000001 microg/ml.

EXAMPLE 7

Hemostimulating Effect

The test was designed to study hemodepression induced by 5-fluorouracil injected i.p. in a dose 175 mg per kg (172 male CBA-mice). Treatment: peptide HM897 was administered i.p. starting from 4th day after 5-FU injection in doses 0.00001, 0.001, 0.01, 1.0 mg/kg for 5 days.

Treatment of controls: normal saline i.p. for 5 days.

Tested parameters: peripheral blood count and bone marrow differential count.

Principal findings: The peptide use promotes active restoration of hemopoiesis. This resulted in normalization of leukocytes and all CBC parameters. In bone marrow the peptide causes restoration of cellularity normalization of all lines of hemopoiesis. The peptide was active starting form 0.001 mg/kg.

EXAMPLE 8

This example demonstrates the effectiveness of the pharmaceutical preparations containing the peptide Glu-Lys (EK) for the treatment of infection. Mice inoculated with lethal doses of methicillin resistant *Staphylococcus aureus* were shown to have markedly enhanced survival when treated with the pharmaceutical preparation.

Animals were inoculated intraperitoneally with 10×LD50 of a *Staphylococcus aureus* suspended in brain-heart infusion broth containing 5 percent mucin. Ampicillin was administered s.c., i.p., or p.o., one hour following bacterial inoculation and deaths occurring during the subsequent three days are recorded. The infecting organisms were Ampicillin-resistant. If significant prevention of mortality (>50 percent survival) was observed, the minimum effective dose (MED) was determined.

Previous studies using methicillin-resistant *S. aureus* (MR) revealed that the MED for Ampicillin is much greater than 100 mg/kg for s.c. administration in the hour subsequent to inoculation.

Two control experiments were initially conducted. EK was administered as a pretreatment prior to microbial inoculation. No antibiotic was administered to this group. The number of survivors at 72 hours was determined. In the second control experiment, saline was administered in the pretreatment regimen, and Ampicillin was administered i.p., at the MED, in the hour following inoculation with the microbe. No EK was administered. The number of survivors at 72 hours was recorded. The influence of EK on survival in the presence of Ampicillin, and in the absence of Ampicillin, after administration of *S. aureus* was determined by conducting experiments in the following manner.

EK was administered in a pretreatment regimen protocol to all animals except the control groups receiving saline alone or ampicillin and saline. The influence of EK was determined over a range of concentrations of 10, 100, and 1000 μg/kg with single daily i.p. administrations for 3 days after which the mice were administered the normally lethal 10×LD50 *S. aureus*. Survival statistics were determined over the periods of 12, 24, 36, 48, and 72 hours. The potential synergistic activity between EK and Ampicillin was determined by administering EK in the pretreatment period, and then 1 hour after inoculum administering Ampicillin. Survival statistics were determined over the periods 12, 23, 36, 48, and 72 hours. FIG. 1 illustrates the experimental protocol.

Intraperitoneal administration of *S. aureus* at 10 times the LD50 resulted in rapid deterioration of animals due to acute peritonitis. All animals in the control group receiving saline alone perished, and the efficacy of EK was determined by comparisons of groups treated with EK to controls receiving saline alone or Ampicillin and saline.

Bacterial culture experiments revealed that EK provides no inhibitory nor suppressive activity on microbial growth over the range of concentrations exceeding 1000 times the administered dose to animals.

Figure 2:
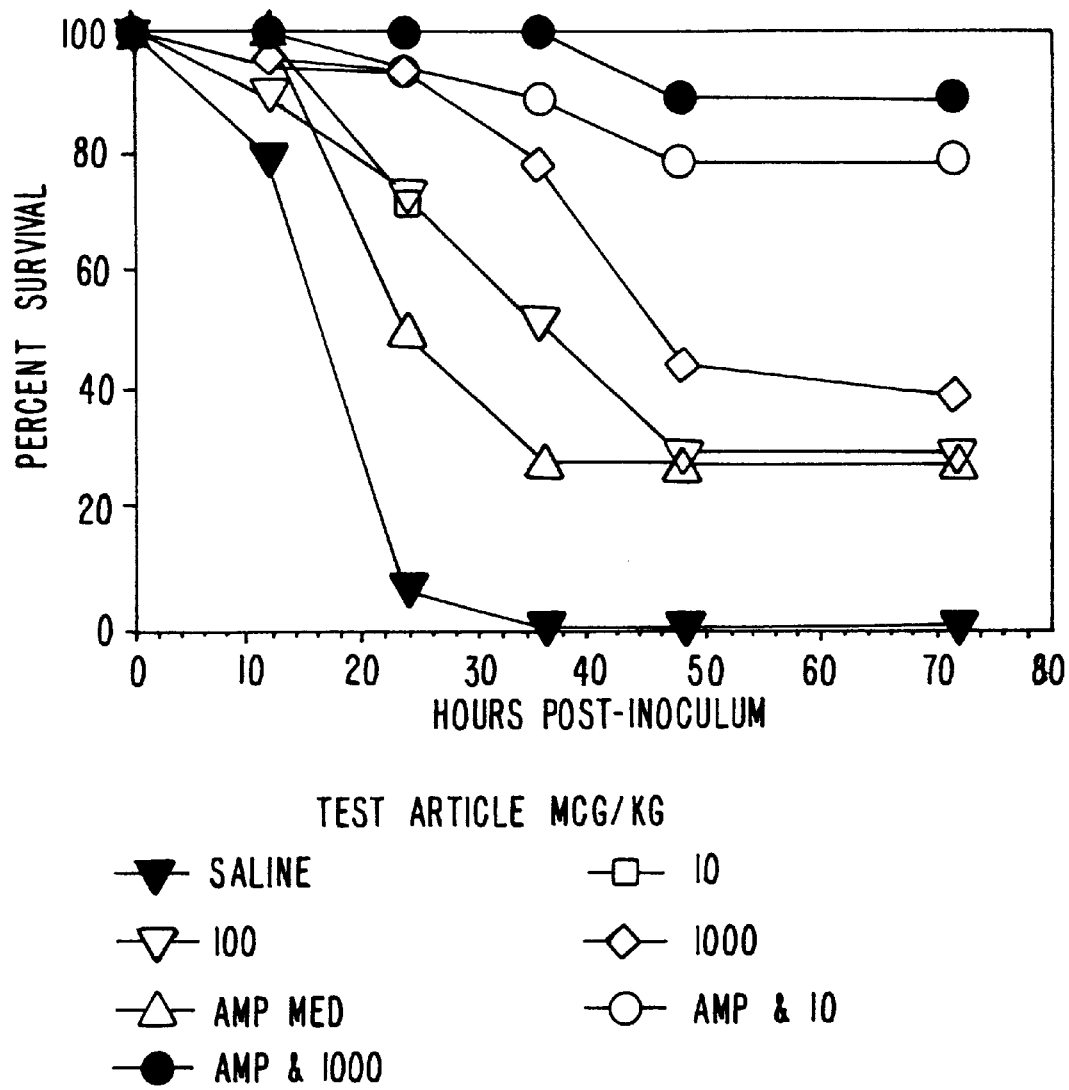
FIG. 2 illustrates survival of bacterially-infected mice treated with EK with and without an adjuvant antibiotic.

The results are summarized in Tables 1–5. Animals administered EK were protected. In the control group there were no survivors at 24 hours. In marked contrast, as many as 78% of the EK treated groups survived at 36 hours. The effect of co-administration of Ampicillin resulted in at least 88% survival at 36 hours compared to only 28% survival if Ampicillin was administered alone. FIG. 2 illustrates this data. By 72 hours at least 27% of the animals receiving only EK were alive, and at least 77% were alive if treated with both Ampicillin and EK.

Administration of EK to mice who are subsequently inoculated with a normally lethal i.p. dose of *S. aureus* results in a dramatic improvement in survival. Moreover, the administration of Ampicillin to mice pre-treated with EK results in a further 3-fold increase in survival as compared to either treatment with Ampicillin or EK alone. If neither peptide or Ampicillin was administered, all animals died.

Figure 3:
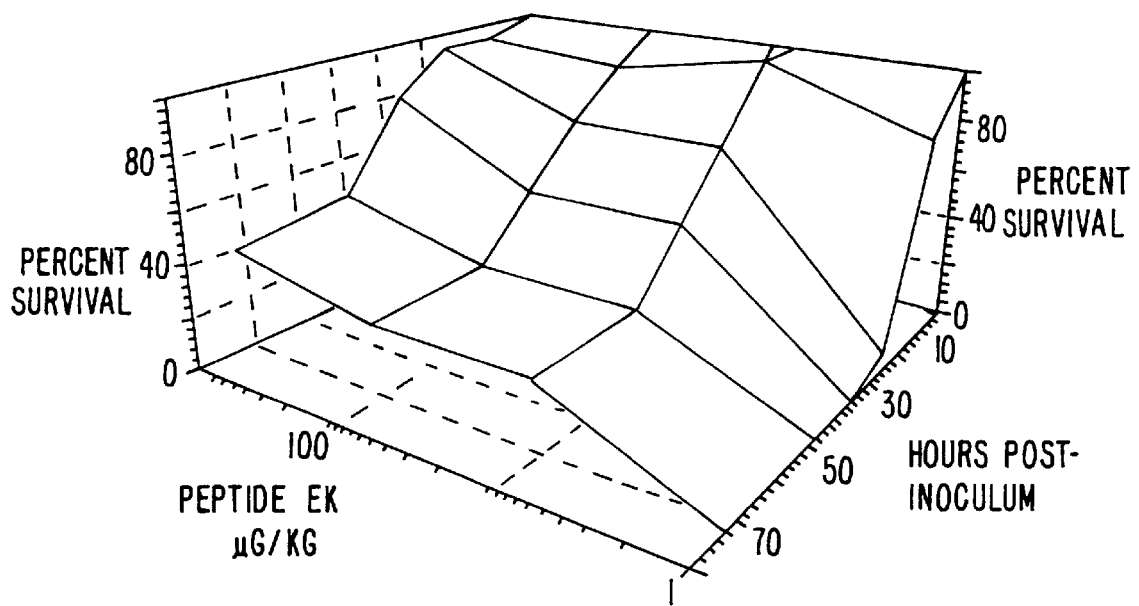
FIG. 3 illustrates survival of bacterially-infected mice treated with EK without adjuvant antibiotics.
Figure 4:
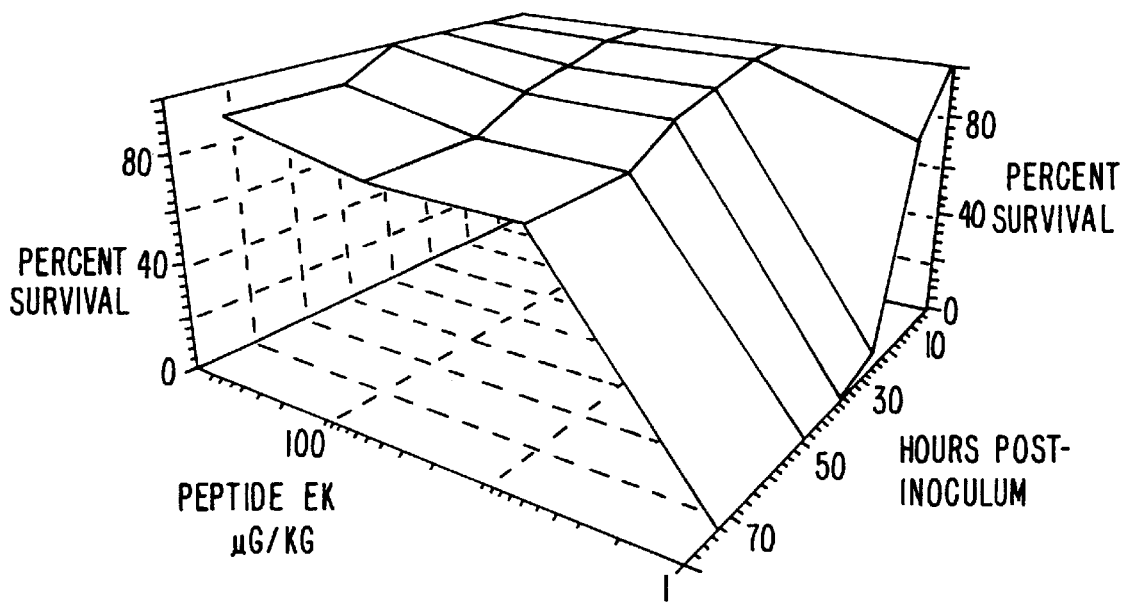
FIG. 4 illustrates survival of bacterially-infected mice treated with EK with adjuvant antibiotics.

These results are summarized in Tables 1–5 below. FIGS. 3 and 4 graphically illustrate the efficacy of treatment of infections with EK.

TABLE 1

Survival Statistics 12 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| control | — | 18 | 4 | 14 | 77.78 | — | — | — |
| EK | 10 | 18 | 0 | 18 | 100.00 | P < 0.05 | n/s | — |
| EK | 100 | 18 | 2 | 16 | 88.89 | n/s | n/s | — |
| EK | 1000 | 18 | 1 | 17 | 94.44 | n/s | n/s | — |
| Amp | MED | 18 | 0 | 18 | 100.00 | P < 0.05 | — | — |
| EK Amp | 10 | 18 | 0 | 18 | 100.00 | P < 0.05 | n/s | n/s |
| EK Amp | 100 | 18 | 0 | 18 | 100.00 | P < 0.05 | n/s | n/s |
| EK Amp | 1000 | 18 | 0 | 18 | 100.00 | P < 0.05 | n/s | n/s |

TABLE 2

Survival Statistics 24 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| EK | 10 | 18 | 5 | 13 | 72.22 | P < 0.001 | n/s | — |
| EK | 100 | 18 | 5 | 13 | 72.22 | P < 0.001 | n/s | — |
| EK | 1000 | 18 | 1 | 17 | 94.44 | P < 0.001 | P < 0.05 | — |
| Amp | MED | 18 | 9 | 9 | 50.00 | P < 0.05 | — | — |
| EK Amp | 10 | 18 | 1 | 17 | 94.44 | P < 0.001 | P < 0.05 | n/s |
| EK Amp | 100 | 18 | 1 | 17 | 94.44 | P < 0.001 | P < 0.05 | n/s |
| EK Amp | 1000 | 18 | 0 | 18 | 100.00 | P < 0.001 | P < 0.05 | n/s |

TABLE 3

Survival Statistics 36 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| EK | 10 | 18 | 9 | 9 | 50.00 | P < 0.05 | n/s | — |
| EK | 100 | 18 | 9 | 9 | 50.00 | P < 0.05 | n/s | — |
| EK | 1000 | 18 | 4 | 14 | 77.78 | P < 0.001 | P < 0.05 | — |
| Amp | MED | 18 | 13 | 5 | 27.78 | P < 0.05 | — | — |
| EK Amp | 10 | 18 | 2 | 16 | 88.89 | P < 0.001 | P < 0.001 | P < 0.05 |
| EK Amp | 100 | 18 | 2 | 16 | 88.89 | P < 0.001 | P < 0.001 | P < 0.05 |
| EK Amp | 1000 | 18 | 0 | 18 | 100.00 | P < 0.001 | P < 0.001 | P < 0.05 |

35

TABLE 4

Survival Statistics 48 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| EK | 10 | 18 | 13 | 5 | 27.78 | P < 0.05 | n/s | — |
| EK | 100 | 18 | 13 | 5 | 27.78 | P < 0.05 | n/s | — |
| EK | 1000 | 18 | 10 | 8 | 44.44 | P < 0.05 | n/s | — |
| Amp | MED | 18 | 13 | 5 | 27.78 | P < 0.05 | — | — |
| EK Amp | 10 | 18 | 4 | 14 | 77.78 | P < 0.001 | P < 0.05 | P < 0.05 |
| EK Amp | 100 | 18 | 4 | 14 | 77.78 | P < 0.001 | P < 0.05 | P < 0.05 |
| EK Amp | 1000 | 18 | 2 | 16 | 88.89 | P < 0.001 | P < 0.001 | P < 0.05 |

TABLE 5

Survival Statistics 72 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| EK | 10 | 18 | 13 | 5 | 27.78 | P < 0.05 | n/s | — |

TABLE 5-continued

Survival Statistics 72 HOURS after Inoculation with *S. aureus*

| Test article | Dose (mcg/kg) | Total | Deaths | Survivors | Survival (%) | Chi-square statistics compared to: | | |
|---|---|---|---|---|---|---|---|---|
| | | | | | | Control | AA | CD |
| EK | 100 | 18 | 13 | 5 | 27.78 | P < 0.05 | n/s | — |
| EK | 1000 | 18 | 11 | 7 | 38.89 | P < 0.05 | n/s | — |
| Amp | MED | 18 | 13 | 5 | 27.78 | P < 0.05 | — | — |
| EK Amp | 10 | 18 | 4 | 14 | 77.78 | P < 0.001 | P < 0.05 | P < 0.05 |
| EK Amp | 100 | 18 | 4 | 14 | 77.78 | P < 0.001 | P < 0.05 | P < 0.05 |
| EK Amp | 1000 | 18 | 2 | 16 | 38.89 | P < 0.001 | P < 0.001 | P < 0.05 |

EXAMPLE 9

This example demonstrates the efficacy of pharmaceutical preparations containing the peptide Thr-Ala-Glu-Glu-Lys (SEQ ID NO:34) (HM897) for the treatment of infection. Mice inoculated with lethal doses of methicillin-resistant *Staphylococcus aureus* were shown to have markedly enhanced survival when treated with the pharmaceutical preparation, although HM897 alone appears to have no measurable specific antibiotic activity (MIC values>1000) in petri culture experiments.

As in Example 8, animals were inoculated intraperitoneally with 10×LD50 of a methicillin-resistant *S. aureus* suspended in brain-heart infusion broth containing 5 percent mucin. Different treatments were administered s.c., i.p., or p.o., one hour later and deaths occurring during the subsequent three days were recorded. If significant prevention of mortality (>50 percent survival) was observed, the minimum effective dose (MED) was determined. As described above, in *S. aureus* (MR), the MED for Ampicillin is much greater than 100 mg/kg for s.c. administration in the hour subsequent to inoculation.

Two control experiments were conducted. HM897 was administered as a pretreatment prior to microbial inoculation, and saline was administered i.p. The number of survivors at 72 hours was determined. In the second control experiment, saline was administered in the pretreatment regimen, and Ampicillin was administered i.p., at the MED, in the hour following inoculation with microbe. The number of survivors at 72 hours was recorded. The influence of HM897 on survival in the presence of Ampicillin, and in the absence of Ampicillin, after administration of *S. aureus* (MR), was determined as follows.

Figure 5:
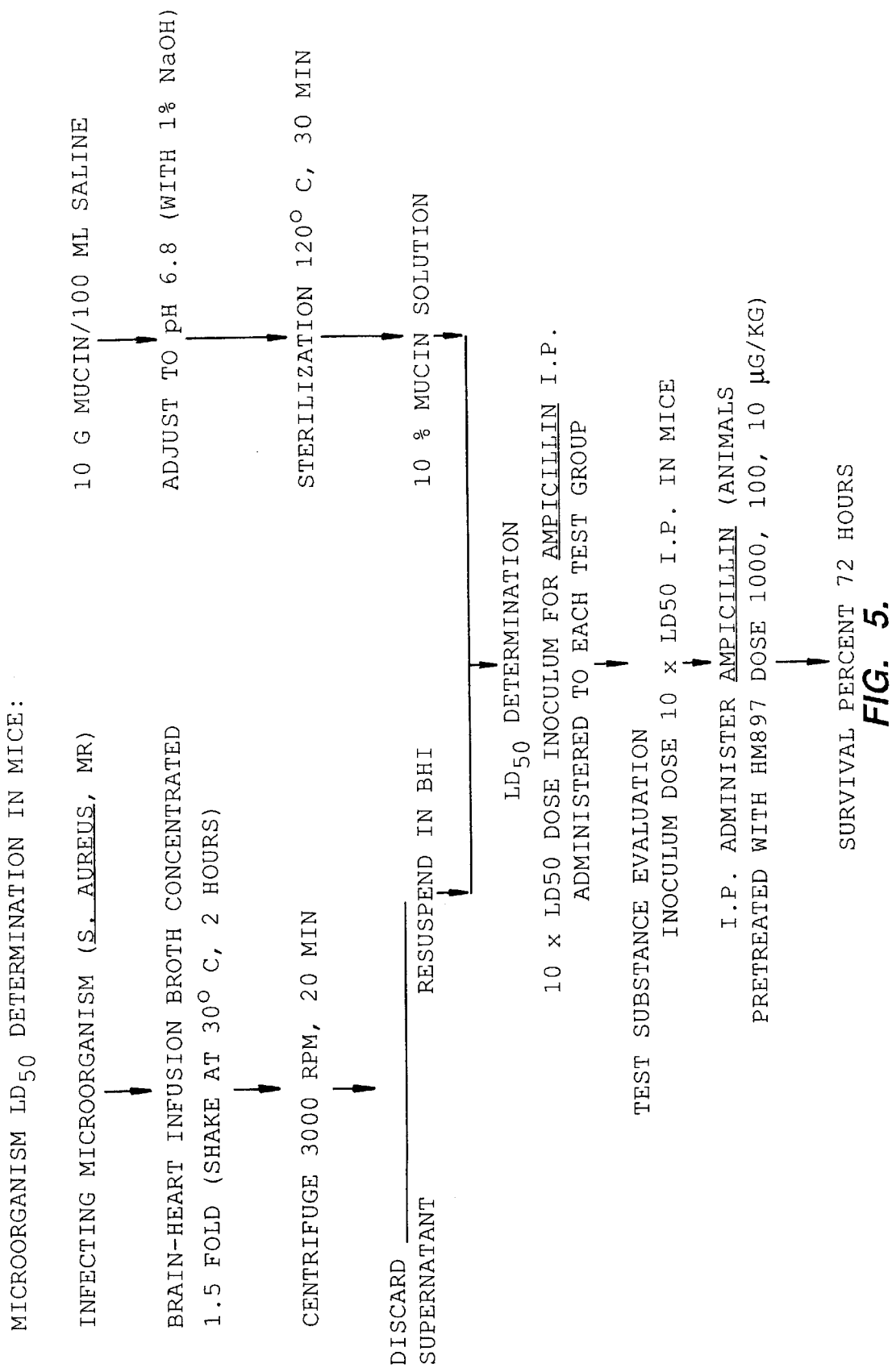
FIG. 5 illustrates an experimental protocol to assess the efficacy of HM897 in the treatment of bacterial infection in mice.

HM897 was administered in a pretreatment regimen protocol to all animals except the control groups provided with either saline alone or Ampicillin and saline. The effect of HM897 treatment was determined over a range of concentrations of 10, 100, and 1000 μg/kg with single daily i.p. administrations for 3 days after which the mice were administered the normally lethal 10×LD50 *S. aureus*. Survival statistics were determined over the periods of 12, 24, 36, 48, and 72 hours. The potential synergistic activity between HM897 and ampicillin was determined by administering HM897 in the pretreatment period, and administering ampicillin 1 hour following the microbial inoculum. Survival statistics were determined over periods of 12, 23, 36, 48, and 72 hours. The method of conducting the experiment is illustrated in FIG. 5.

Administration of 10 times the LD50 inoculum resulted in rapid deterioration of animals due to acute peritonitis. All animals in the control group receiving saline alone died and the efficacy of HM897 treatment was determined by comparisons of HM897-treated groups to saline and ampicillin treated control groups in which no HM897 was administered.

The results of the experiment are summarized in Tables 6–10 below. Animals receiving HM897 exhibited increased survival. In the control group receiving saline alone, there were less than 6% survivors by 24 hours, and no survivors by 36 hours. As many of 61 percent of the HM897-treated groups at 36 hours. The effect of co-administration of Ampicillin resulted in 77% to 94% survival at 36 hours compared to only 28% survival in the group receiving ampicillin alone. By 72 hours 22–39% of the animals receiving HM897 alone were alive, and 72–94% survived if treated with ampicillin and HM897.

Figure 6:
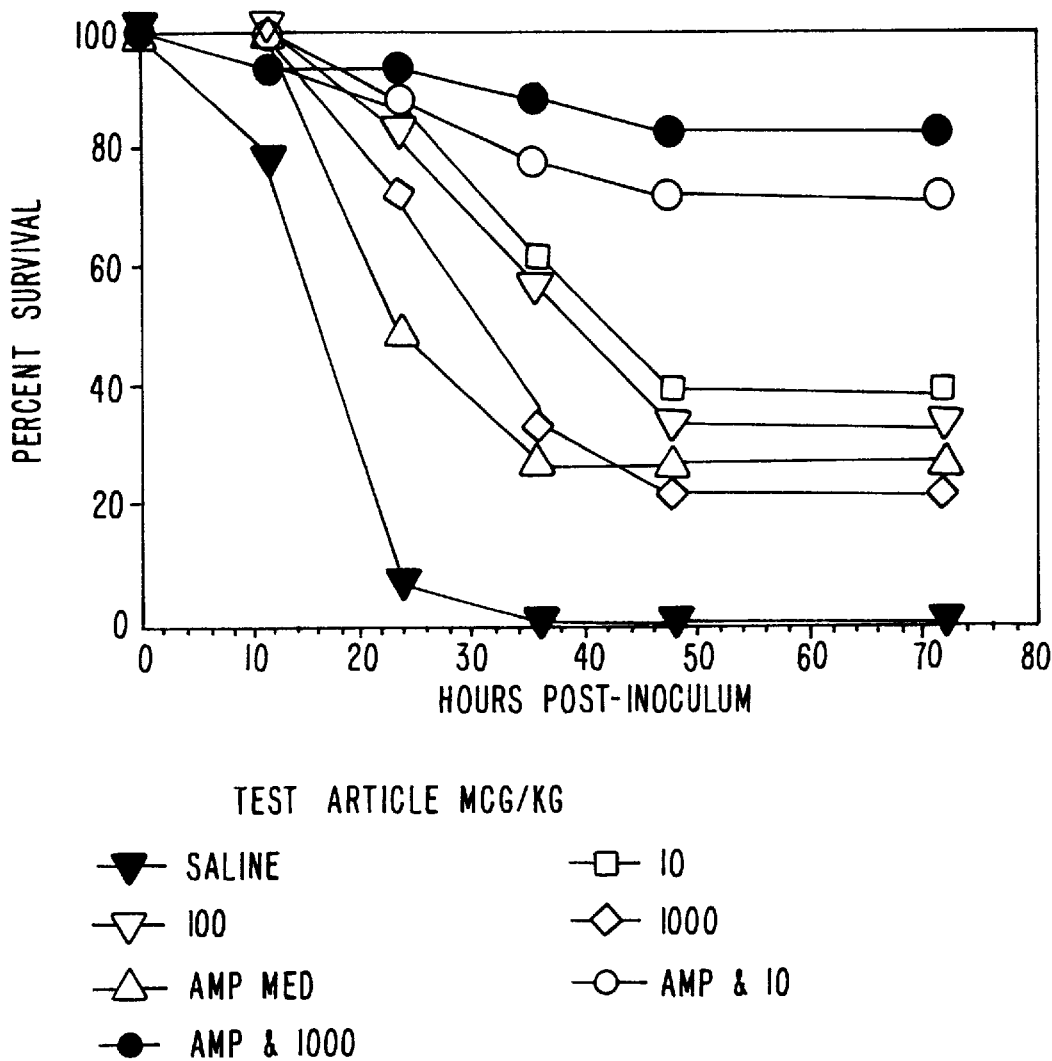
FIG. 6 illustrates survival of bacterially-infected mice treated with HM897 with and without adjuvant antibiotics.
Figure 7:
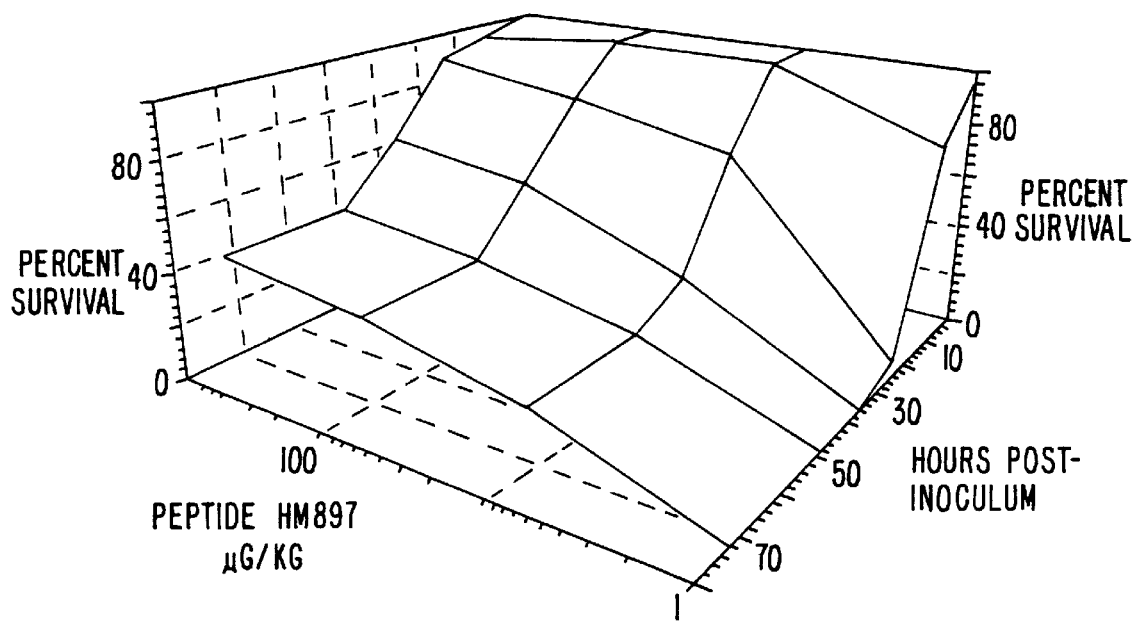
FIG. 7 illustrates survival of bacterially-infected mice treated with HM897 with adjuvant antibiotics.
Figure 8:
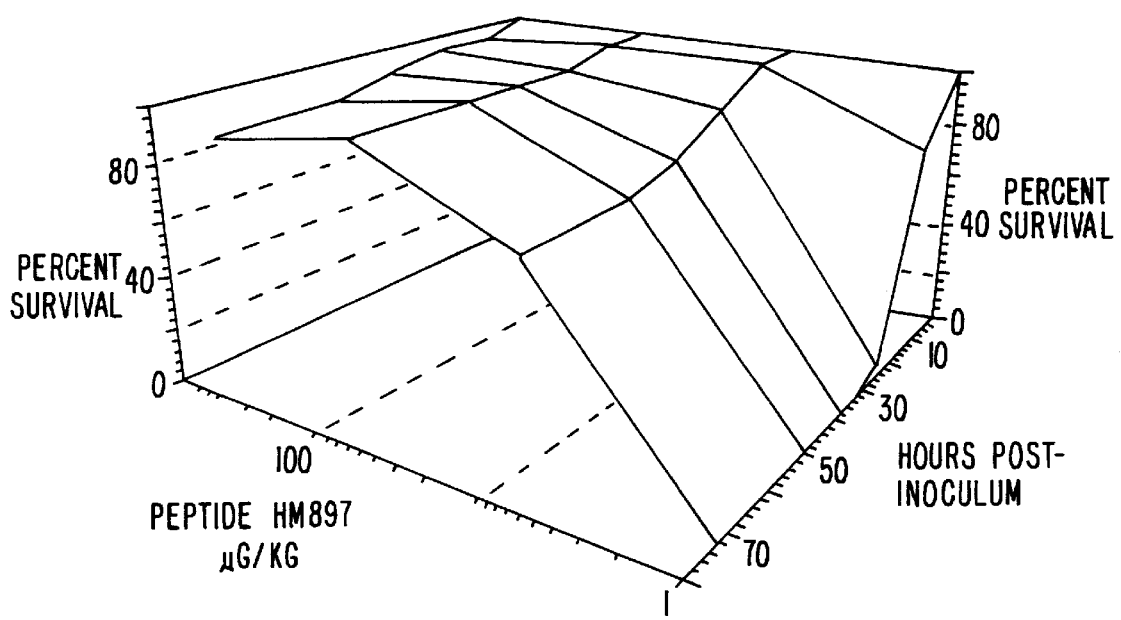
FIG. 8 illustrates survival of bacterially-infected mice treated with HM897 without adjuvant antibiotics.

Administration of HM897 to mice that are subsequently inoculated with a normally lethal i.p. dose of *S. aureus* provided a dramatic improvement in survival. Moreover, the administration of ampicillin to mice pre-treated with HM897 resulted in a further 2-fold increase in survival as compared to either Ampicillin or HM897 administration alone. If neither HM897 or ampicillin were administered, all animals died. FIGS. 6–8 below. Comparison of FIGS. 7 and 8 reveal dramatic differences in survival for mice that received co-administration of Ampicillin in a single dose accompanying HM897 administration. This demonstrates a dramatic synergistic effect between HM897 and ampicillin.

TABLE 6

Survival Statistics 12 HOURS after Inoculation with *S. aureus*

| Test article | Dose (mcg/kg) | Total | Deaths | Survivors | Survival (%) | Chi-square statistics compared to: | | |
|---|---|---|---|---|---|---|---|---|
| | | | | | | Control | AA | CD |
| Control | — | 18 | 4 | 14 | 77.78 | — | — | — |
| HM897 | 10 | 18 | 0 | 18 | 100.00 | P < 0.05 | n/s | — |
| HM897 | 100 | 18 | 0 | 18 | 100.00 | P < 0.05 | n/s | — |

TABLE 6-continued

Survival Statistics 12 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| HM897 | 1000 | 18 | 1 | 17 | 94.44 | n/s | n/s | — |
| Amp | MED | 18 | 0 | 18 | 100.00 | P < 0.05 | — | — |
| HM897 Amp | 10 | 18 | 0 | 18 | 100.00 | P < 0.05 | n/s | n/s |
| HM897 Amp | 100 | 18 | 0 | 18 | 100.00 | P < 0.05 | n/s | n/s |
| HM897 Amp | 1000 | 18 | 1 | 178 | 94.44 | n/s | n/s | n/s |

TABLE 7

Survival Statistics 24 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 17 | 1 | 5.56 | — | — | — |
| HM897 | 10 | 18 | 5 | 13 | 72.22 | P < 0.001 | n/s | — |
| HM897 | 100 | 18 | 3 | 15 | 83.33 | P < 0.001 | P < 0.05 | — |
| HM897 | 1000 | 18 | 2 | 16 | 88.89 | P < 0.001 | P < 0.05 | — |
| Amp | MED | 18 | 9 | 9 | 50.00 | P < 0.05 | — | — |
| HM897 Amp | 10 | 18 | 2 | 16 | 88.89 | P < 0.001 | P < 0.05 | n/s |
| HM897 Amp | 100 | 18 | 1 | 17 | 94.44 | P < 0.001 | P < 0.05 | n/s |
| HM897 Amp | 1000 | 18 | 1 | 17 | 94.44 | P < 0.001 | P < 0.05 | n/s |

TABLE 8

Survival Statistics 36 HOURS after Inoculation with *S. aureus*

| Test article | Dose (mcg/kg) | Total | Deaths | Survivors | Survival (%) | Chi-square statistics compared to: Control | AA | CD |
|---|---|---|---|---|---|---|---|---|
| Control | — | 18 | 18 | 0 | 0.00 | — | — | — |
| HM897 | 10 | 18 | 12 | 6 | 33.33 | P < 0.001 | n/s | — |
| HM897 | 100 | 18 | 8 | 10 | 55.56 | P < 0.001 | n/s | — |
| HM897 | 1000 | 18 | 7 | 11 | 61.11 | P < 0.001 | P < 0.05 | — |
| Amp | MED | 18 | 13 | 5 | 27.78 | P < 0.05 | — | — |
| HM897 Amp | 10 | 18 | 4 | 14 | 77.78 | P < 0.001 | P < 0.05 | P < 0.05 |
| HM897 Amp | 100 | 18 | 1 | 17 | 94.44 | P < 0.001 | P < 0.001 | P < 0.05 |
| HM897 Amp | 1000 | 18 | 2 | 16 | 88.89 | P < 0.001 | P < 0.001 | n/s |

TABLE 9

Survival Statistics 48 HOURS after Inoculation with *S. aureus*

| Test article | Dose (mcg/kg) | Total | Deaths | Survivors | Survival (%) | Control | AA | CD |
|---|---|---|---|---|---|---|---|---|
| Control | — | 18 | 18 | 0 | 0.00 | — | — | — |
| HM897 | 10 | 18 | 14 | 4 | 22.22 | $P < 0.05$ | n/s | — |
| HM897 | 100 | 18 | 12 | 6 | 33.33 | $P < 0.05$ | n/s | — |
| HM897 | 1000 | 18 | 11 | 7 | 38.89 | $P < 0.05$ | n/s | — |
| Amp | MED | 18 | 13 | 5 | 27.78 | $P < 0.05$ | — | — |
| HM897 Amp | 10 | 18 | 5 | 13 | 72.22 | $P < 0.001$ | $P < 0.05$ | $P < 0.05$ |
| HM897 Amp | 100 | 18 | 1 | 17 | 94.44 | $P < 0.001$ | $P < 0.001$ | $P < 0.001$ |
| HM897 Amp | 1000 | 18 | 3 | 15 | 83.33 | $P < 0.001$ | $P < 0.05$ | $P < 0.05$ |

TABLE 10

Survival Statistics 72 HOURS after Inoculation with *S. aureus*

| Test article | Dose (mcg/kg) | Total | Deaths | Survivors | Survival (%) | Control | AA | CD |
|---|---|---|---|---|---|---|---|---|
| Control | — | 18 | 18 | 0 | 0.00 | — | — | — |
| HM897 | 10 | 18 | 14 | 4 | 22.22 | $P < 0.05$ | n/s | — |
| HM897 | 100 | 18 | 12 | 6 | 33.33 | $P < 0.05$ | n/s | — |
| HM897 | 1000 | 18 | 11 | 7 | 38.89 | $P < 0.05$ | n/s | — |
| Amp | MED | 18 | 13 | 5 | 27.78 | $P < 0.05$ | — | — |
| HM897 Amp | 10 | 18 | 5 | 13 | 72.22 | $P < 0.001$ | $P < 0.05$ | $P < 0.05$ |
| HM897 Amp | 100 | 18 | 1 | 17 | 94.44 | $P < 0.001$ | $P < 0.001$ | $P < 0.001$ |
| HM897 Amp | 1000 | 18 | 3 | 15 | 83.33 | $P < 0.001$ | $P < 0.05$ | $P < 0.05$ |

EXAMPLE 10

This example demonstrates the augmentation of a vaccine by administration of a peptide Thr-Ala-Glu-Glu-Lys (SEQ ID NO:34) (HM897). Administration of HM897 following vaccination provided enhanced protection against infection.

The present investigation was performed in hatchling fish. In these animals, the lymphoid system is poorly developed, with demonstrable immune incompetence. Hatchlings exposed to certain antigens prior to maturation, instead of responding by producing antibodies, are blocked with the induction of "negative" immunity, failing to subsequently respond to antigen stimulation. The effects of such blocking may last several weeks, with a subsequent loss of memory resulting in more mature fish that are highly susceptible to future infection.

A number of non-specific factors have been observed in the fish ova, including C-reactive protein-like precipitins, and lecithin-like agglutinins, and some fish immunoglobulins (Ig) suggesting that passive immunity may be provided by the parent in some species of fish. Passive immunity has not been observed in salmonids.

The major lymphoid organs in teleost fish are the thymus, kidney, and spleen. The thymus is composed of developing lymphocytes, and as in other vertebrates, it is regarded as the pool of virgin lymphocytes which subsequently emigrate to join the pool of peripheral cells of the circulation and lymphoid organs.

The thymus is the first lymphoid organ to develop lymphocytes in hatchlings, and in rainbow trout, the fully differentiated thymus is separated from the external environment only by a single layer of epithelial cells, which possess pores up to 20 μm in diameter. These epithelial fenestrations are observed to close in older fish.

Lymphoid cells first appear in the blood and lymphoid trout within 3 days of hatching. The rate of growth of the lymphoid tissues exceeds the rest of the body's rate of growth in the first few weeks of life. The weight of the lymphoid organs relative to the body weight teaches a peak at 2 months of age when the trout are normally 0.5 grams; thereafter the relative weights diminish. An intense period of mitotic activity occurs within the thymus during these first few months. Thymic involution appears to occur after approximately 9 months.

Morphologically identifiable lymphocytes are seen in early hatchlings, and the T- and B-lymphocytes develop at different speeds. The majority of cells have no surface immunoglobulins prior to 48 days, and the ability to produce antibody prior to this age is unlikely. This suggests that B-cells and T-suppressors become functionally active at about 4 weeks of age, and T-helper cell functions mature later at about 8 weeks of age.

In the present investigation, fish were obtained and inoculated at approximately 12 weeks of age. Immunologic studies were conducted under a variety of conditions in which fish were provided with vaccination to observe vaccine augmentation, and under conditions in which no vaccine was provided prior to inoculum. The effects of exposure time, HM897 concentration, and vaccine on mortalities relative to control studies in which no HM897 was administered provided data for analysis of the immunologic effect of HM897.

A study was carried out by Bio-Research Laboratories (BRL) to determine if HM897 possesses immune enhancing properties using a fish disease model. The study was conducted using Rainbow trout (*Oncorhynchus mykiss*) to compare the effects of a standard fish vaccine to the protection provided by varying dosages of HM897. The fish were challenged with *Vibrio anquillarum* (V-775), a bacteria that causes fatal vibriosis, typically 3–5 days following pathogen exposure.

Rainbow Trout (*Oncorhynchus mykiss*) weighing approximately 5 grams were used as test organisms. The fish were obtained from Cran-Mar Trout Farm. Upon arrival at BRL's facility, the fish were quarantined for a minimum of seven days, and observed to be disease free. During this period, the fish were held at a stable temperature. There was consistent water quality in an aerated flow-through system with a flow rate of approximately 30 liters per hour. During the holding period the fish were observed daily for signs of disease, stress, injury, hemorrhaging, and external parasite. The fish were not fed 48 hours prior to testing.

BRL's facilities included an area for holding and acclimating fish while providing a constant temperature of (16±2° C.) using carbon filtered tap water. The air used for aeration was free of oil and fumes. The test fish were shielded from any disturbances. The facility was well ventilated and free of fumes. There was a 16-hour light and 8-hour dark photoperiod. Special care was taken to prevent contamination of the fish holding tanks.

The test holding chambers were located in a special room with the temperature remaining constant at 12±1° C. Each test chamber was 11"×21"×10". The test chambers were cleaned thoroughly before using. A standard cleaning procedure was followed. Detergent or acetone was used to remove organic compounds; 5% concentration of nitric acid was used to remove metals and bases; and 200 mg hypochlorite/L was used for disinfection. Finally, the test chambers were rinsed with dilution water before the start of the test.

The Rainbow trout used in this study weighed an average of 5 grams. The fish were divided into 21 groups with 50 fish per group. Each group of 50 fish was maintained in two 10-gallon tanks (25 fish/tank).

The dosage level for the challenge bacteria *Vibrio anquillarum* (V-775) was determined by running multiple levels of bacterial dilutions designed to kill 25 to 100% of unvaccinated fish (LD25 to LD100). The level of bacterial dilution to achieve a LD75 (the level designed to kill 75% of the non-vaccinated fish) was a dilution of $10^{-4}$ to $10^{-5}$. The challenge bacteria were grown for 48 hours at 25° C. in trypticase soy broth. The $10^{-4}$ dilution was made from this broth in 0.9% saline. All fish excepting the control group that received no bacterial challenge were inoculated 7 days after exposure to HM897.

HM897 was provided as a powder. The following concentrations of HM897 were made per each 38 L tank; 2.5 µg/38L, 10 µg/38L, 25 µg/38L, 50 µg/38L, 75 µg/38L, 100 µg/38L, 150 µg/38L, and 250 µg/38L.

Rainbow trout hatchling were exposed to the concentration of HM897 as described below. Some of the fish had been vaccinated while others had received no vaccination. In each tank, fifty vaccinated or unvaccinated fish were exposed for a period of 5 minutes to HM897, and then removed and placed in an assigned tank according to the group number.

The positive control group (III) received a vaccine made from *Vibrio anquillarum* (V-775). This was made through a fermentation and extraction process in the BRL laboratory facility and is equivalent to the aquaculture industry standard vibrio vaccine.

All groups scheduled to be challenged with the *Vibrio anguillarum* bacterium were challenged at the LD75 dilution on day seven of the experiment by i.p. injection of 0.1 mL of $10^{-4}$ bacterial dilution. The fish were observed daily for mortalities.

The experimental groups were as follows:

Group I:
Fifty unvaccinated fish were placed in Group I, and observed for three weeks. These fish did not receive treatment with HMS897 and were not challenged with bacteria.

Group II:
Fifty unvaccinated fish were exposed to $10^{-4}$ dilution of *Vibrio anquillarum* (V-775) on day 7 of the experiment and observed for mortality. This group was not vaccinated and did not receive HM897.

Group III:
Fifty fish were vaccinated on day one and exposed to $10^{-4}$ dilution of *Vibrio anguillarum* (V-775) on day 7 day of the experiment. The fish were not treated with HM897.

Group IVa:
On day one, fifty vaccinated fish were allowed to swim in a tank containing 38 liters of water with 2.5 µg of HM897 for 5 minutes and then they were placed in the tanks marked Group IVa. On day 7 the fish were exposed to $10^{-4}$ dilution of *Vibrio anquillarum* (V-775) and observed for mortality.

Group IVb:
On day one, fifty vaccinated fish were allowed to swim in a tank containing 38 liters of water with 10 µg of HM897 for 5 minutes and then they were placed in the tanks marked Group IVb. On day 7 the fish were exposed to $10^{-4}$ dilution of *Vibrio anquillarum* (V-775) and observed for mortality.

Group IVc:
On day one, fifty vaccinated fish were allowed to swim in a tank containing 38 liters of water with 50 pg of HM897 for 5 minutes and then they were placed in the tanks marked Group IVc. On day 7 the fish were exposed to $10^{-4}$ dilution of *Vibrio anquillarum (V-775)* and observed for mortality.

Group IVd:
On day one, fifty vaccinated fish were allowed to swim in a tank containing 38 liters of water with 100 µg of HM897 for 5 minutes and then they were placed in the tanks marked Group IVd. On day 7 the fish were exposed to $10^{-4}$ dilution of *Vibrio anquillarum* (V-775) and observed for mortality.

Group Va:
On day one, fifty unvaccinated fish were allowed to swim in a tank containing 38 liters of water with 10 µg of HM897 for 5 minutes and then they were placed in the tanks marked Group Va. On day 7 the fish were exposed to $10^{-4}$ dilution of *Vibrio anquillarum* (V-775) and observed for mortality.
Group Vb:

On day one, fifty unvaccinated fish were allowed to swim in a tank containing 38 liters of water with 25 $\mu$g of HM897 for 5 minutes and then they were placed in the tanks marked Group Vb. On day 7 the fish were exposed to $10^{-4}$ dilution of *Vibrio anquillarum* (V-775) and observed for mortality.
Group Vc:

On day one, fifty unvaccinated fish were allowed to swim in a tank containing 38 liters of water with 75 $\mu$g of HM897 for 5 minutes and then they were placed in the tanks marked Group Vc. On day 7 the fish were exposed to $10^{-4}$ dilution of *Vibrio anguillarum* (V-775) and observed for mortality.
Group Vd:

On day one, fifty unvaccinated fish were allowed to swim in a tank containing 38 liters of water with 150 $\mu$g of HM897 for 5 minutes and then they were placed in the tanks marked Group Vd. On day 7 the fish were exposed to $10^{-4}$ dilution of *Vibrio anquillarum* (V-775) and observed for mortality.
Group Ve:

On day one, fifty unvaccinated fish were allowed to swim in a tank containing 38 liters of water with 250 $\mu$g of HM897 for 5 minutes and then they were placed in the tanks marked Group Ve. On day 7 the fish were exposed to $10^{-4}$ dilution of *Vibrio anquillarum* (V-775) and observed for mortality.

All of the groups were observed for a period of twenty-one days, and the effect of the treatments were evaluated based on the number of fish mortalities. The groups are summarized in Table XI-1 below.

TABLE XI-1

Summary Of Experimental Design for HM897 and Retromedine ™ Immunologic Studies in Rainbow Trout.

| Group | Vaccinated Day 1 | Test Article | Test Article $\mu$g 38 liters Day 1 | Inoculated LD75 Day 7 | Number of Fish |
|---|---|---|---|---|---|
| I | no | none | none | no | 50 |
| II | no | none | none | yes | 50 |
| III | yes | none | none | yes | 50 |
| IVa | yes | HM897 | 2.5 | yes | 50 |
| IVb | yes | HM897 | 10 | yes | 50 |
| IVc | yes | HM897 | 50 | yes | 50 |
| IVd | yes | HM897 | 100 | yes | 50 |
| Va | no | HM897 | 10 | yes | 50 |
| Vb | no | HM897 | 25 | yes | 50 |
| Vc | no | HM897 | 75 | yes | 50 |
| Vd | no | HM897 | 150 | yes | 50 |
| Ve | no | HM897 | 250 | yes | 50 |

The bacterial challenge (*Vibrio anquillarum*, V-775) dilution levels and daily accumulated mortalities are shown in Table XI-2. The results of this experiment established the LD75 of the challenge bacterial. Each group of fifteen fish were challenged with bacterial dilution of $10^{-2}$, $10^{-3}$, $10^{-4}$, or $10^{-5}$. Nine days after injection of the bacterial dilutions the accumulated mortalities were as follows:

At $10^{-2}$ bacterial dilution 14 fish were dead (93.3% mortality).

At $10^{-3}$ bacterial dilution 13 fish were dead (86.7% morality).

At $10^{-4}$ bacterial dilution 10 fish were dead (66.7% mortality).

At $10^{-5}$ bacterial dilution 10 fish were dead (66.7% mortality).

TABLE XI-2

Cumulative Mortalities for Rainbow Trout Inoculated with *Vibrio anguillarum* LD75 Determination.

| Group | Dilation | Number of Fish | 06/30 | 07/01 | 07/02 | 07/03 | 07/04 | 07/05 | 07/06 | 07/07 | 07/08 | 07/09 |
|---|---|---|---|---|---|---|---|---|---|---|---|---|
| 1 | 10-2 | 15 | 0 | 0 | 14 | 14 | 14 | 14 | 14 | 14 | 14 | 14 |
| 2 | 10-3 | 15 | 0 | 0 | 6 | 9 | 13 | 13 | 13 | 13 | 13 | 13 |
| 3 | 10-4 | 15 | 0 | 0 | 0 | 5 | 9 | 10 | 10 | 10 | 10 | 10 |
| 4 | 10-5 | 15 | 0 | 0 | 0 | 4 | 7 | 10 | 10 | 10 | 10 | 10 |

The daily accumulated mortalities are shown in Table XI-3. The number of the mortalities for each group were as follows:

Group I: This group had no mortalities.

Group II: Thirty-one fish died from bacterial infection (62% mortality).

Group III: Fifteen fish died from bacterial infection (30% mortality).

Group IVa: Thirteen fish died from bacterial infection (26% mortality).

Group IVb: Seven fish died from bacterial infection (14% mortality).

Group IVc: Ten fish died from bacterial infection (20% mortality).

Group IVd: Seventeen fish died from bacterial infection (34% mortality).

Group Va: Thirty-three fish died from bacterial infection (66% mortality).

Group Vb: Thirty-tree fish died from bacterial infection (66% mortality).

Group Vc: Thirty-four fish died from bacterial infection (68% mortality).

Group Vd: Thirty-two fish died from bacterial infection (64% mortality).

Group Ve: Thirty-four fish died from bacterial infection (68% mortality).

TABLE XI-3

Summary Cumulative Mortalities for HM897 Influence on Rainbow Trout Infected with *Vibrio Anguillarum*

| Group | \multicolumn{13}{c}{Day} | Total Mortalities |
|---|---|---|---|---|---|---|---|---|---|---|---|---|---|---|
| | 1 | 2.10 | 11 | 12 | 13 | 14 | 15 | 16 | 17 | 18 | 19 | 20 | 21 | |
| I | 0 | 0 | 0 | 0 | 0 | 0 | 0 | 0 | 0 | 0 | 0 | 0 | 0 | 0 |
| II | 0 | 0 | 0 | 0 | 22 | 27 | 29 | 31 | 31 | 31 | 31 | 31 | 31 | 31 |
| III | 0 | 0 | 0 | 0 | 8 | 14 | 14 | 15 | 15 | 15 | 15 | 15 | 15 | 15 |
| IVa | 0 | 0 | 0 | 0 | 1 | 7 | 10 | 13 | 13 | 13 | 13 | 13 | 13 | 13 |
| IVb | 0 | 0 | 0 | 0 | 1 | 5 | 6 | 6 | 7 | 7 | 7 | 7 | 7 | 7 |
| IVc | 0 | 0 | 0 | 0 | 1 | 5 | 10 | 10 | 10 | 10 | 10 | 10 | 10 | 10 |
| IVd | 0 | 0 | 0 | 0 | 8 | 15 | 16 | 17 | 17 | 17 | 17 | 17 | 17 | 17 |
| Va | 0 | 0 | 0 | 0 | 16 | 24 | 28 | 33 | 33 | 33 | 33 | 33 | 33 | 33 |
| Vb | 0 | 0 | 0 | 0 | 18 | 25 | 32 | 33 | 33 | 33 | 33 | 33 | 33 | 33 |
| Vc | 0 | 0 | 1 | 1 | 21 | 29 | 32 | 33 | 34 | 34 | 34 | 34 | 34 | 34 |
| Vd | 0 | 0 | 0 | 0 | 14 | 23 | 28 | 32 | 32 | 32 | 32 | 32 | 32 | 32 |
| Ve | 0 | 0 | 0 | 0 | 14 | 25 | 30 | 32 | 34 | 34 | 34 | 34 | 34 | 34 |

TABLE XI-4

Summary Of Results Trout Mortalities

| Group | Vaccinated Day 1 | Test Article | Test Article μg 38 liters Day 1 | Inoculated LD75 Day 7 | Total Mortalities | Percent Mortalities |
|---|---|---|---|---|---|---|
| I | no | None | none | no | 0 | 0 |
| II | no | None | none | yes | 31 | 62 |
| III | yes | Vaccine | none | yes | 15 | 30 |
| IVa | yes | HM897 | 2.5 | yes | 13 | 26 |
| IVb | yes | HM897 | 10 | yes | 7 | 14 |
| IVc | yes | HM897 | 50 | yes | 10 | 20 |
| IVd | yes | HM897 | 100 | yes | 17 | 34 |
| Va | no | HM897 | 10 | yes | 33 | 66 |
| Vb | no | HM897 | 25 | yes | 33 | 66 |
| Vc | no | HM897 | 75 | yes | 34 | 68 |
| Vd | no | HM897 | 150 | yes | 32 | 64 |
| Ve | no | HM897 | 250 | yes | 34 | 68 |

*Vibrio anquillarum* (V-775) was used as challenge bacteria at $10^{-4}$ dilution. The bacterial challenge study (Table XI-2) revealed that $10^{-4}$ and $10^{-5}$ of the bacterial dilutions can kill about 75% of the infected fish (LD75). The $10^{-4}$ dilution was selected as a LD75 bacterial dilution.

Group I, without any treatment and with no bacterial challenge, had no mortalities. This confirmed that the fish were in good health. Adequate filtration and aeration were provided to maintain a suitable environment for the fish.

No mortalities in Group I and 62% mortalities in Group II clearly indicate that all the mortalities were related to the bacterial infection (Table XI-4). The bacterial dilution was predicted to kill about 75% of the fish, and the actual mortality of control group (Group II) was 62%.

A typical commercial vaccine usually affords 60% to 70% protection. The vaccinated group (Group III) showed 30% mortalities and therefore provided 70% protection against the challenge bacteria.

Figure 9:
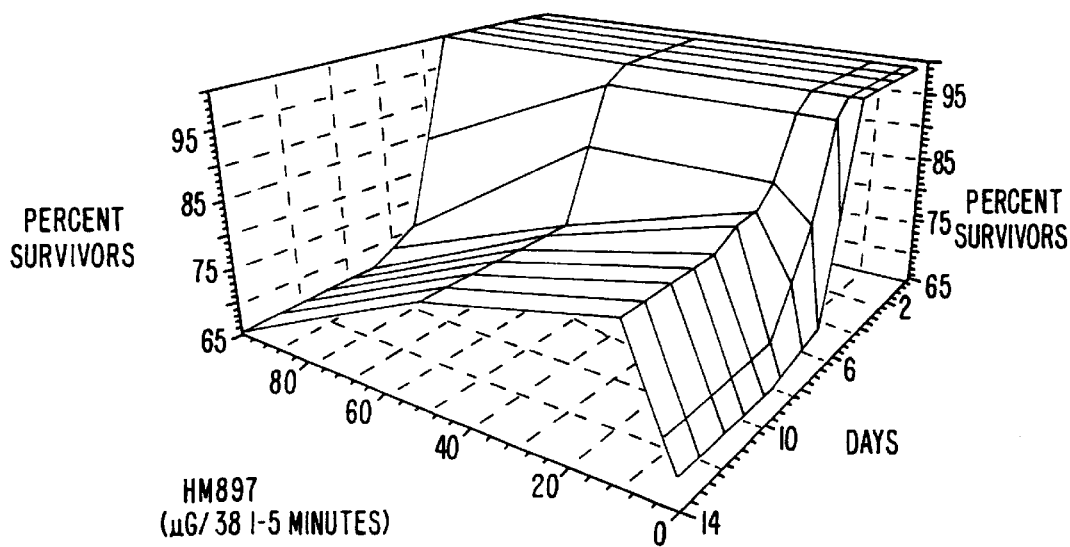
FIG. 9 illustrates survival of vaccinated fish treated with different amounts of HM897.

The fish in groups IVa, IVb, IVc, and IVd were vaccinated and then each exposed to a different concentrations of HM897 for 5 minutes. Each group reveals a different level of protection against the challenge bacteria. The fish in Group IVb with 10 μg of HM897 in 38 liters for 5 minutes inoculated with challenge *Vibrio anquillarum* 7 days after vaccination had the lowest mortalities at 14% compared to the group receiving vaccine alone at 30% (FIG. 9).

Figure 10:
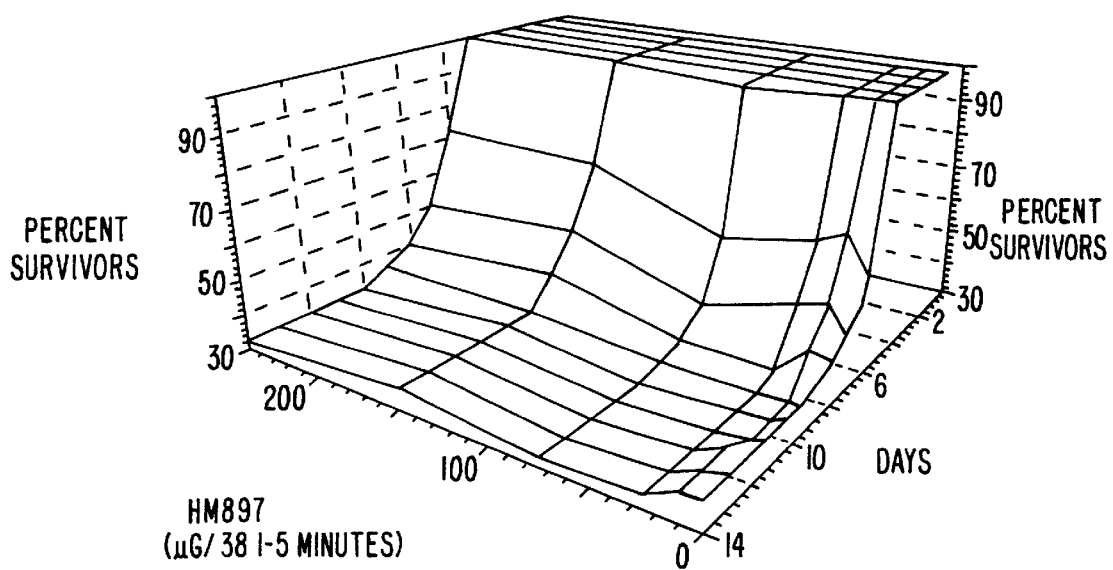
FIG. 10 illustrates survival of unvaccinated fish treated with different amounts of HM897.

The groups treated with different levels of HM897 exposure without vaccine (Groups Va to Ve) showed no protection against the bacterial infection (Table XI-3, FIG. 10). The percentage of the fish mortalities in these groups were similar to the control group (Group II) in which no treatment was provided excepting challenge with *Vibrio anguillarum*. This indicates that HM897 has a statistically significant effect for augmentation of vaccinations.

All publications, patents and patent applications mentioned in this specification are herein incorporated by reference into the specification to the same extent as if each individual publication, patent or patent application was specifically and individually indicated to be incorporated herein by reference.

Although the foregoing invention has been described in some detail by way of illustration and example for purposes of clarity of understanding, it will be obvious that certain changes and modifications may be practiced within the scope of the appended claims.

What is claimed is:

1. A method for modulating the activity of a host's immune system comprising administering to the host a therapeutically effective dose of an isolated peptide of at least five amino acids of the formula R'-Glx-Glx-Lys-R" (SEQ ID NO:1) or a pharmaceutically acceptable salt thereof, wherein:

R' is H- or a first amino acid sequence selected from Thr-Pro-, Thr-Ala-, Ser-Ala-, Ser-Pro-, Ser-Ser- and Leu-Thr-Ala-;

Glx is Glu or Gln;

R" is -H or a second amino acid sequence selected from -Ala, -Ala-Ala or -Ala-Val;

and wherein the peptide is not Thr-Ala-Glx-Glx-Lys (SEQ ID NO:4).

2. The method of claim 1 wherein the amino acids are L-amino) acids.

3. The method of claim 2 wherein the host is a human.

4. The method of claim 2 wherein the host is a non-human animal.

5. The method of claim 2 wherein the peptide is Thr-Pro-Glx-Glx-Lys (SEQ ID NO:8).

6. The method of claim 2 wherein the peptide is Thr-Pro-Glu-Glu-Lys (SEQ ID NO:33).

7. The method of claim 2 wherein the peptide is Thr-Pro-Gln-Gln-Lys (SEQ ID NO:41).

8. The method of claim 2 wherein R" is -H.

9. The method of claim 2 wherein R' is Thr-Pro-.

10. The method of claim 2 wherein the peptide is Leu-Thr-Ala-Glx-Glx-Lys-Ala (SEQ ID NO:29), Leu-Thr-Ala-Glx-Glx-Lys-Ala-Ala (SEQ ID NO:30) or Leu-Thr-Ala-Glx-Glx-Lys-Ala-Val (SEQ ID NO:31).

11. The method of claim 3 comprising administering the peptide to an immunodeficient or immunodepressed host.

12. The method of claim 3 comprising administering the peptide to a host with a hyperactive immune state.

13. The method of claim 3 wherein the peptide is administered parenterally.

14. The method of claim 3 wherein the peptide is administered orally.

15. The method of claim 3 wherein the peptide is administered intranasally, intravenously or intramuscularly.

16. The method of claim 3 wherein the peptide is administered in the form of a pharmaceutical composition comprising the peptide and an aqueous pharmaceutically acceptable carrier.

17. The method of claim 3 wherein the peptide is Thr-Pro-Glx-Glx-Lys (SEQ ID NO:8) and the dose is about 0.1 mg/kg per day to about 1000 mg/kg per day.

18. The method of claim 3 wherein the peptide is Thr-Pro-Glx-Glx-Lys (SEQ ID NO:8) and the dose is about 0.25 mg/kg per day to about 100 mg/kg per day.

19. The method of claim 3 wherein the peptide is Thr-Pro-Glx-Glx-Lys (SEQ ID NO:8) and the dose is about 0.5 mg/kg per day to about 20 mg/kg per day.

20. The method of claim 3 wherein the peptide is Thr-Pro-Glx-Glx-Lys (SEQ ID NO:8) and the dose is about 0.7 mg/kg per day to about 10 mg/kg per day.

21. A method for modulating the activity of a host's immune system comprising Administering to the host a therapeutically effective dose of an isolated peptide of at least five amino acids of the formula Thr-Ala-Glx-Glx-Lys (SEQ ID NO:4) or a pharmaceutically acceptable salt thereof, wherein Glx is Glu or Gln.

22. The method of claim 21 wherein the amino acids are L- amino acids.

23. The method of claim 22 wherein the host is a human.

24. The method of claim 22 wherein the host is a non-human animal.

25. The method of claim 22 wherein the peptide is Thr-Ala-Glu-Glu-Lys (SEQ ID NO:34).

26. The method of claim 22 wherein the peptide is Thr-Ala-Gln-Gln-Lys (SEQ ID NO:42).

27. The method of claim 23 comprising administering the peptide to an immunodeficient or immunodepressed host.

28. The method of claim 23 comprising administering the peptide to a host with a hyperactive immune state.

29. The method of claim 23 wherein the peptide is administered parenterally.

30. The method of claim 23 wherein the peptide is administered orally.

31. The method of claim 23 wherein the peptide is administered intranasally, intravenously or intramuscularly.

32. The method of claim 23 wherein the peptide is administered in the form of a pharmaceutical composition comprising the peptide and an aqueous pharmaceutically acceptable carrier.

33. The method of claim 23 wherein the dose is about 0.1 mg/kg per day to about 1000 mg/kg per day.

34. The method of claim 23 wherein the dose is about 0.25 mg/kg per day to about 100 mg/kg per day.

35. The method of claim 23 wherein the dose is about 0.5 mg/kg per day to about 20 mg/kg per day.

36. The method of claim 23 wherein the dose is about 0.7 mg/kg per day to about 10 mg/kg per day.

* * * * *

```
                          SEQUENCE LISTING (1) GENERAL INFORMATION:

(iii) NUMBER OF SEQUENCES: 42

(2) INFORMATION FOR SEQ ID NO:1:

(i) SEQUENCE CHARACTERISTICS:
         (A) LENGTH: 15 amino acids
         (B) TYPE: amino acid
         (C) STRANDEDNESS:
         (D) TOPOLOGY: linear (ii) MOLECULE TYPE: peptide (ix) FEATURE:
         (A) NAME/KEY: Modified-site
         (B) LOCATION: 1..6
         (D) OTHER INFORMATION: /product= "OTHER"
             /note= "Xaa may be present or absent,
             with the proviso that the peptide
             sequence is at least 5 and not more
             than 9 amino acids"

(ix) FEATURE:
         (A) NAME/KEY: Modified-site
         (B) LOCATION: 10..15
         (D) OTHER INFORMATION: /product= "OTHER"
             /note= "Xaa may be present or absent,
             with the proviso that the peptide
             sequence is at least 5 and not more
             than 9 amino acids"

(xi) SEQUENCE DESCRIPTION: SEQ ID NO:1:

Xaa Xaa Xaa Xaa Xaa Xaa Glx Glx Lys Xaa Xaa Xaa Xaa Xaa Xaa
1               5                   10                  15

(2) INFORMATION FOR SEQ ID NO:2:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:2:

Glx Glx Lys Ala Ala
1               5

(2) INFORMATION FOR SEQ ID NO:3:

(i) SEQUENCE CHARACTERISTICS:
         (A) LENGTH: 5 amino acids
         (B) TYPE: amino acid
         (C) STRANDEDNESS:
         (D) TOPOLOGY: linear (ii) MOLECULE TYPE: peptide (xi) SEQUENCE DESCRIPTION: SEQ ID NO:3:

Glx Glx Lys Ala Val
1               5

(2) INFORMATION FOR SEQ ID NO:4:

(i) SEQUENCE CHARACTERISTICS:
         (A) LENGTH: 5 amino acids
         (B) TYPE: amino acid
```

```
            (C) STRANDEDNESS:
            (D) TOPOLOGY: linear (ii) MOLECULE TYPE: peptide (xi) SEQUENCE DESCRIPTION: SEQ ID NO:4:

Thr Ala Glx Glx Lys
1               5

(2) INFORMATION FOR SEQ ID NO:5:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:5:

Thr Ala Glx Glx Lys Ala
1               5

(2) INFORMATION FOR SEQ ID NO:6:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:6:

Thr Ala Glx Glx Lys Ala Ala
1               5

(2) INFORMATION FOR SEQ ID NO:7:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:7:

Thr Ala Glx Glx Lys Ala Val
1               5

(2) INFORMATION FOR SEQ ID NO:8:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:8:

Thr Pro Glx Glx Lys
1               5

(2) INFORMATION FOR SEQ ID NO:9:

(i) SEQUENCE CHARACTERISTICS:
            (A) LENGTH: 6 amino acids
```

```
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:9:

Thr Pro Glx Glx Lys Ala
1               5

(2) INFORMATION FOR SEQ ID NO:10:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:10:

Thr Pro Glx Glx Lys Ala Ala
1               5

(2) INFORMATION FOR SEQ ID NO:11:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:11:

Thr Pro Glx Glx Lys Ala Val
1               5

(2) INFORMATION FOR SEQ ID NO:12:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:12:

Ser Ala Glx Glx Lys
1               5

(2) INFORMATION FOR SEQ ID NO:13:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:13:

Ser Ala Glx Glx Lys Ala
1               5

(2) INFORMATION FOR SEQ ID NO:14:

(i) SEQUENCE CHARACTERISTICS:
```

```
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:14:

Ser Ala Glx Glx Lys Ala Ala
1               5

(2) INFORMATION FOR SEQ ID NO:15:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:15:

Ser Ala Glx Glx Lys Ala Val
1               5

(2) INFORMATION FOR SEQ ID NO:16:

(i) SEQUENCE CHARACTERISTICS:
            (A) LENGTH: 5 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:16:

Ser Pro Glx Glx Lys
1               5

(2) INFORMATION FOR SEQ ID NO:17:

(i) SEQUENCE CHARACTERISTICS:
            (A) LENGTH: 6 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:17:

Ser Pro Glx Glx Lys Ala
1               5

(2) INFORMATION FOR SEQ ID NO:18:

(i) SEQUENCE CHARACTERISTICS:
            (A) LENGTH: 7 amino acids
            (B) TYPE: amino acid
            (C) STRANDEDNESS:
            (D) TOPOLOGY: linear (ii) MOLECULE TYPE: peptide (xi) SEQUENCE DESCRIPTION: SEQ ID NO:18:

Ser Pro Glx Glx Lys Ala Ala
1               5

(2) INFORMATION FOR SEQ ID NO:19:
```

(i) SEQUENCE CHARACTERISTICS:
           (A) LENGTH: 7 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:19:

Ser Pro Glx Glx Lys Ala Val
1               5

(2) INFORMATION FOR SEQ ID NO:20:

(i) SEQUENCE CHARACTERISTICS:
           (A) LENGTH: 5 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:20:

Ser Ser Glx Glx Lys
1               5

(2) INFORMATION FOR SEQ ID NO:21:

(i) SEQUENCE CHARACTERISTICS:
           (A) LENGTH: 6 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:21:

Ser Ser Glx Glx Lys Ala
1               5

(2) INFORMATION FOR SEQ ID NO:22:

(i) SEQUENCE CHARACTERISTICS:
           (A) LENGTH: 7 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:22:

Ser Ser Glx Glx Lys Ala Ala
1               5

(2) INFORMATION FOR SEQ ID NO:23:

(i) SEQUENCE CHARACTERISTICS:
           (A) LENGTH: 7 amino acids
           (B) TYPE: amino acid
           (C) STRANDEDNESS:
           (D) TOPOLOGY: linear (ii) MOLECULE TYPE: peptide (xi) SEQUENCE DESCRIPTION: SEQ ID NO:23:

Ser Ser Glx Glx Lys Ala Val
1               5

(2) INFORMATION FOR SEQ ID NO:24:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:24:

Met Leu Thr Ala Glx Glx Lys
1               5

(2) INFORMATION FOR SEQ ID NO:25:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:25:

Met Leu Thr Ala Glx Glx Lys Ala
1               5

(2) INFORMATION FOR SEQ ID NO:26:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:26:

Met Leu Thr Ala Glx Glx Lys Ala Ala
1               5

(2) INFORMATION FOR SEQ ID NO:27:

(i) SEQUENCE CHARACTERISTICS:
        (A) LENGTH: 9 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:27:

Met Leu Thr Ala Glx Glx Lys Ala Val
1               5

(2) INFORMATION FOR SEQ ID NO:28:

(i) SEQUENCE CHARACTERISTICS:
        (A) LENGTH: 6 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:28:

Leu Thr Ala Glx Glx Lys
1               5

```
(2) INFORMATION FOR SEQ ID NO:29:

(i) SEQUENCE CHARACTERISTICS:
        (A) LENGTH: 7 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:29:

Leu Thr Ala Glx Glx Lys Ala
1               5

(2) INFORMATION FOR SEQ ID NO:30:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:30:

Leu Thr Ala Glx Glx Lys Ala Ala
1               5

(2) INFORMATION FOR SEQ ID NO:31:

(i) SEQUENCE CHARACTERISTICS:
        (A) LENGTH: 8 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:31:

Leu Thr Ala Glx Glx Lys Ala Val
1               5

(2) INFORMATION FOR SEQ ID NO:32:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:32:

Met Leu Thr Ala
1

(2) INFORMATION FOR SEQ ID NO:33:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:33:

Thr Pro Glu Glu Lys
1               5
```

(2) INFORMATION FOR SEQ ID NO:34:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:34:

Thr Ala Glu Glu Lys
1           5

(2) INFORMATION FOR SEQ ID NO:35:

(i) SEQUENCE CHARACTERISTICS:
        (A) LENGTH: 14 amino acids
        (B) TYPE: amino acid
        (C) STRANDEDNESS:
        (D) TOPOLOGY: linear (ii) MOLECULE TYPE: peptide (ix) FEATURE:
        (A) NAME/KEY: Modified-site
        (B) LOCATION: 1..6
        (D) OTHER INFORMATION: /product= "OTHER"
            /note= "Xaa may be present or absent,
            with the proviso that the peptide
            sequence is at least 2 and not more
            than 9 amino acids"

(ix) FEATURE:
        (A) NAME/KEY: Modified-site
        (B) LOCATION: 9..14
        (D) OTHER INFORMATION: /product= "OTHER"
            /note= "Xaa may be present or absent,
            with the proviso that the peptide
            sequence is at least 2 and not more
            than 9 amino acids"

(xi) SEQUENCE DESCRIPTION: SEQ ID NO:35:

Xaa Xaa Xaa Xaa Xaa Xaa Glx Lys Xaa Xaa Xaa Xaa Xaa Xaa
1           5               10

(2) INFORMATION FOR SEQ ID NO:36:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:36:

Glx Lys Ala Ala
1

(2) INFORMATION FOR SEQ ID NO:37:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:37:

```
Glx Lys Ala Val
1

(2) INFORMATION FOR SEQ ID NO:38:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:38:

Met Leu Thr Ala Glx
1               5

(2) INFORMATION FOR SEQ ID NO:39:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:39:

Leu Thr Ala Glx
1

(2) INFORMATION FOR SEQ ID NO:40:

(i) SEQUENCE CHARACTERISTICS:
        (A) LENGTH: 4 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:40:

Glx Glx Lys Ala
1

(2) INFORMATION FOR SEQ ID NO:41:

(i) SEQUENCE CHARACTERISTICS:
        (A) LENGTH: 5 amino acids
        (B) TYPE: amino acid
        (C) STRANDEDNESS:
        (D) TOPOLOGY: linear (ii) MOLECULE TYPE: peptide (xi) SEQUENCE DESCRIPTION: SEQ ID NO:41:

Thr Pro Gln Gln Lys
1               5

(2) INFORMATION FOR SEQ ID NO:42:

(i) SEQUENCE CHARACTERISTICS:
        (A) LENGTH: 5 amino acids
        (B) TYPE: amino acid
        (C) STRANDEDNESS:
        (D) TOPOLOGY: linear
```

-continued (ii) MOLECULE TYPE: peptide (xi) SEQUENCE DESCRIPTION: SEQ ID NO:42:

```
Thr Ala Gln Gln Lys
1               5
```